US012753383B2

(12) United States Patent
Numano et al.

(10) Patent No.: US 12,753,383 B2

(45) Date of Patent: Oct. 6, 2026

(54) ELECTROPORATION DEVICE AND METHOD FOR PRODUCING CELLS WITH INTRODUCED FOREIGN SUBSTANCE

(71) Applicant: NATIONAL UNIVERSITY CORPORATION TOYOHASHI UNIVERSITY OF TECHNOLOGY, Toyohashi (JP)

(72) Inventors: Rika Numano, Toyohashi (JP); Ryuto Shinozaki, Toyohashi (JP)

(73) Assignee: NATIONAL UNIVERSITY CORPORATION TOYOHASHI UNIVERSITY OF TECHNOLOGY, Toyohashi (JP)

( * ) Notice: Subject to any disclaimer, the term of this patent is extended or adjusted under 35 U.S.C. 154(b) by 1353 days.

(21) Appl. No.: 17/415,798

(22) PCT Filed: Dec. 19, 2019

(86) PCT No.: PCT/JP2019/049952

§ 371 (c)(1),
(2) Date: Jun. 18, 2021

(87) PCT Pub. No.: WO2020/130106

PCT Pub. Date: Jun. 25, 2020

(65) Prior Publication Data

US 2022/0135937 A1 May 5, 2022

(30) Foreign Application Priority Data

Dec. 20, 2018 (JP) ................................ 2018-238147

(51) Int. Cl.
*C12N 1/38* (2006.01)
*B01L 3/00* (2006.01)
(Continued)

(52) U.S. Cl.
CPC .......... *C12N 1/38* (2013.01); *B01L 3/502715* (2013.01); *C12M 35/02* (2013.01);
(Continued)

(58) Field of Classification Search
None
See application file for complete search history.

(56) References Cited

U.S. PATENT DOCUMENTS 5,720,921 A 2/1998 Maserol
6,074,605 A 6/2000 Meserol
(Continued)

FOREIGN PATENT DOCUMENTS

CN 1060418 4/1992
CN 1195997 10/1998
(Continued)

OTHER PUBLICATIONS

Kershaw, J. F. "SAE International's Dictionary for Automotive Engineers", pp. 163-201, 2023. (Year: 2023).*
(Continued)

*Primary Examiner* — Michael A Marcheschi
*Assistant Examiner* — Ashley Lopezlira
(74) *Attorney, Agent, or Firm* — Muncy, Geissler, Olds & Lowe, P.C.

(57) ABSTRACT

An electroporation device includes a holding portion, a discharge generating portion, a conductive portion, and a power amount control portion. The holding portion is configured to hold a solution containing a foreign substance and a cell. The discharge generating portion includes a pair of electrodes disposed at a predetermined gap, and configured to generate an arc discharge between the pair of electrodes. The conductive portion is configured to electrically connect the holding portion and the discharge generating portion, and to supply, to the holding portion, a pulsed electric
(Continued)

current resulting from the arc discharge generated by the discharge generating portion. The power amount control portion is configured to control an amount of electric energy of the pulsed electric current supplied to the holding portion.

16 Claims, 34 Drawing Sheets

(51) Int. Cl.

| | |
|---|---|
| ***C12M 1/42*** | (2006.01) |
| *C12N 15/87* | (2006.01) |

(52) U.S. Cl.

CPC ... *B01L 2200/16* (2013.01); *B01L 2300/0645* (2013.01); *C12N 15/87* (2013.01)

(56) References Cited

U.S. PATENT DOCUMENTS

| | | | | |
|---|---|---|---|---|
| 10,066,199 | B2 | 9/2018 | Mizuno et al. | |
| 2007/0128708 | A1 | 6/2007 | Gamelin | |
| 2007/0275454 | A1 | 11/2007 | Chang | |
| 2008/0058991 | A1* | 3/2008 | Lee | F16K 99/0001 700/282 |
| 2013/0052711 | A1 | 2/2013 | Chen | |
| 2015/0368604 | A1 | 12/2015 | Mizuno et al. | |
| 2016/0159673 | A1 | 6/2016 | Gafri | |
| 2017/0362564 | A1 | 12/2017 | Lamotte | |

FOREIGN PATENT DOCUMENTS

| | | | |
|---|---|---|---|
| CN | 101370927 | | 2/2009 |
| CN | 103060191 | | 4/2013 |
| JP | 2001-187384 | A | 7/2001 |
| JP | 2006149310 | | 6/2006 |
| JP | 2017-104073 | A | 6/2017 |
| JP | 6269968 | B2 | 1/2018 |
| WO | 03057819 | | 7/2003 |
| WO | 2006112870 | | 10/2006 |
| WO | 2014/092164 | A1 | 6/2014 |

OTHER PUBLICATIONS

Kershaw, J. F. “SAE International’s Dictionary for Automotive Engineers”, pp. 435-472, 2023. (Year: 2023).*

Cleveland, C. J., Morris, C., “Dictionary of Energy (Expanded Edition)”, pp. 68-122, 2009. (Year: 2009).*

Tomsic, Joan L., (2000), Dictionary of Materials and Testing (2nd Edition), SAE International, Retrieved from knovel.com (Year: 2000).*

Rebersek M., et al., Generator and setup for emulating exposures of biological samples to lightning strokes, IEEE Transactions on Biomedical Engineering (2015) vol. 62, No. 10, pp. 2535-2543, ISSN:0018-9294.

International Search Report of International Application No. PCT/JP2019/049952 mailed Mar. 17, 2020 and English translation thereof.

Office Action of the corresponding CN application No. 201980084768.2 mailed Nov. 29, 2023 and English translation thereof.

* cited by examiner

ELECTROPORATION DEVICE AND METHOD FOR PRODUCING CELLS WITH INTRODUCED FOREIGN SUBSTANCE

This application is a national stage application under 35 U.S.C. § 371 of PCT Application PCT/JP2019/049952, filed Dec. 19, 2019, which claims benefit to Japanese Patent Application JP2018-238147, filed Dec. 20, 2018; said applications incorporated herein by reference.

TECHNICAL FIELD

The present invention relates to an electroporation device capable of introducing a foreign substance into cells contained in a cell suspension by electroporation, and a method for producing cells with an introduced foreign substance into which the foreign substance has been introduced.

BACKGROUND ART

An electroporation device has been developed (refer to Patent Literature 1, for example) that performs electroporation in a droplet in insulating oil. Electroporation is one method of introducing a foreign substance into cells, the foreign substance being a nucleic acid molecule such as DNA, RNA, and the like, biological material such as a protein and the like, and a chemical compound that is an effective component of a drug and the like. In general electroporation, a high-voltage pulsed electric current is applied to a target cell using a special high-voltage pulse generator, temporarily forming micropores in the cell membrane through which a foreign substance can pass, and thus causing the foreign substance to be captured in the target cell. A device disclosed in Patent Literature 1 performs the electroporation by applying the pulsed electric current of a lower power to the target cell than a previous electroporation device, as a result of a droplet in the insulation oil coming into contact with electrodes when reciprocating between the electrodes. It is reported that the device disclosed in Patent Literature 1 can reduce an amount of samples of the target cells compared to the electroporation device of known art, and can improve a viability of survival of the target cells compared to the electroporation device of known art.

CITATION LIST

Patent Literature

Patent Literature 1: Japanese Laid-Open Patent Publication No. 6269968

SUMMARY OF INVENTION

In a known device of known art that performs electroporation inside a droplet in oil, an operation to recover a sample from the oil after a response is complex.

It is an objective of the present invention to provide an electroporation device and a method for producing cells with an introduced foreign substance, with which, compared to a device that performs electroporation by causing a solution (droplet) containing a foreign substance and cells to reciprocate in oil, an operation to recover a sample after a reaction is simplified.

An electroporation device according to a first aspect of the present invention, includes a holding portion, a discharge generating portion, a conductive portion, and a power amount control portion. The holding portion is configured to hold a solution containing a foreign substance and a cell. The discharge generating portion includes a pair of electrodes disposed at a predetermined gap, and configured to generate an arc discharge between the pair of electrodes. The conductive portion is configured to electrically connect the holding portion and the discharge generating portion, and to supply, to the holding portion, a pulsed electric current resulting from the arc discharge generated by the discharge generating portion. The power amount control portion is configured to control an amount of electric energy of the pulsed electric current supplied to the holding portion.

The electroporation device according to the first aspect can apply the pulsed high-voltage electric current for a short time period to the solution, without causing the solution (a droplet) containing the foreign substance and the cells to reciprocate in oil. Thus, since there is no need to recover the sample from the oil, the electroporation device can simplify an operation to recover the sample after a reaction, in comparison to a device that performs the electroporation in a droplet in oil.

The power amount control portion of the electroporation device according to the first aspect may include a condenser electrically connected to a power supply portion and to the discharge generating portion. The condenser accumulates an electric charge as a result of voltage applied by the power supply portion, and the condenser discharges the accumulated electric charge to the discharge generating portion. The electroporation device can prescribe an amount of electric energy of the pulsed electric current supplied to the holding portion, using the electrostatic capacity of the condenser.

The discharge generating portion of the electroporation device according to the first aspect may be electrically connected to a power supply portion, and the power amount control portion may include a condenser electrically connected to the holding portion, the condenser being configured to accumulate the pulsed electric current supplied to the holding portion. The electroporation device can prescribe the amount of electric energy of the pulsed electric current supplied to the holding portion, using the electrostatic capacity of the condenser.

The power supply portion of the electroporation device according to the first aspect may be configured to supply a high-voltage DC power of 3 kV or more. With the device, there is no need to separately prepare the power supply portion, In the discharge generating portion of the electroporation device according to the first aspect, the predetermined gap may be changeable. The electroporation device can easily change conditions, such as the magnitude of the pulsed electric current supplied to the holding portion. Thus, in the electroporation device, setting of reaction conditions suited to a sample is easy.

Leading ends of the pair of electrodes of the discharge generating portion of the electroporation device according to the first aspect may be formed in a hemispherical shape. In comparison to a case in which the electroporation device includes electrodes having another shape, it is possible to cause the discharge generating portion to generate the arc discharge in a stable manner.

The power amount control portion of the electroporation device according to the first aspect may further include a dark current control portion configured to control a dark current generated in the discharge generating portion. Even when the dark current is generated in the discharge generating portion, the electroporation device can cause the discharge generating portion to generate the arc discharge in the stable manner.

The electroporation device according to the first aspect may further include a cycle adjustment portion configured to cyclically apply a voltage to the discharge generating portion at a predetermined interval. The electroporation device can easily change conditions of a length of an interval and a number of repetitions. Thus, in the electroporation device, it is easy to set reaction conditions suited to the sample.

The power amount control portion according to the first aspect may include an inductor connected in parallel with the holding portion and the condenser. In this case, using the action of the inductor, the electroporation device can apply a voltage to a target cell in both forward and reverse directions, via the holding portion.

The power amount control portion according to the first aspect may include a diode connected in parallel with the holding portion, to consist a forward direction of an electric current discharged from the condenser flows. In this case, in the electroporation device, a waveform of the pulsed electric current that is applied to the holding portion can be caused to be a waveform in which, due to rectification by the diode, a negative component in an attenuated vibration waveform of the pulsed electric current is eliminated.

A method for producing cells with an introduced foreign substance according to a second aspect of the present invention includes the holding process causes a holding portion of the electroporation device according to the first aspect to hold a solution containing a foreign substance and a cell, a supply process of generating a pulsed electric current by arc discharge and supplying the generated pulsed electric current to the holding portion, and a recovery process of recovering, from the holding portion, the solution that has undergone the supply process. According to the method for producing cells with an introduced foreign substance according to the second aspect, the same effects as those of the electroporation device according to the first aspect are achieved.

DESCRIPTION OF EMBODIMENTS

1. Electroporation Device 1, 10

Figure 1:
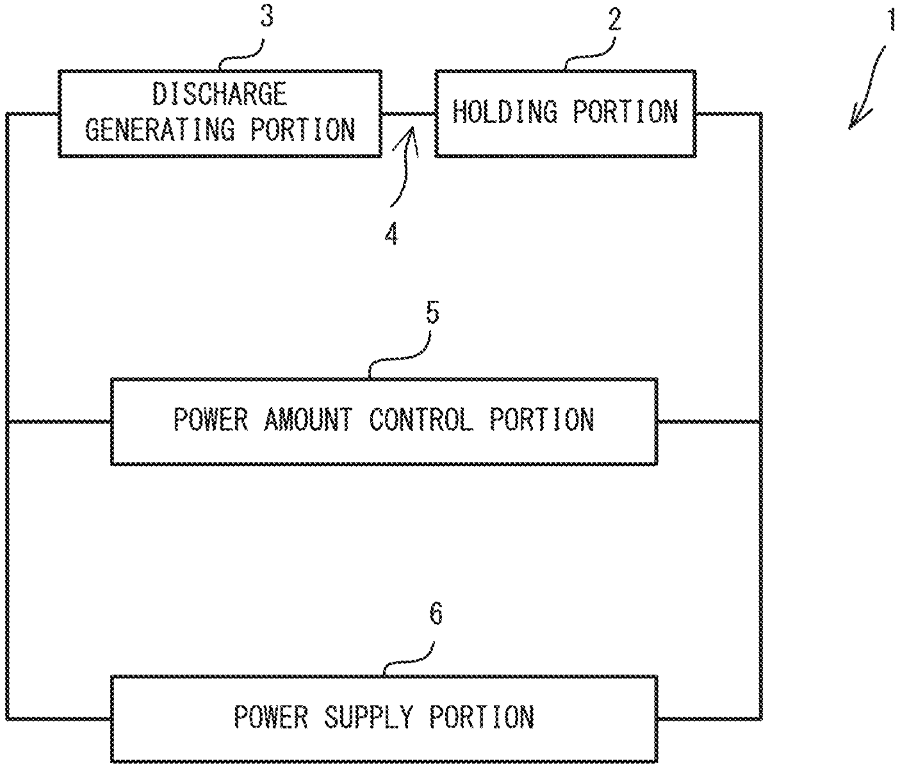
FIG. 1 is a conceptual diagram of an electroporation device 1.

Hereinafter, a preferred embodiment of the present invention will be explained with reference to the drawings. An electroporation device 1, 10 according to the present invention will be explained with reference to FIG. 1 to FIG. 8. The electroporation device 1, 10 (hereinafter also referred to as the device 1, 10) is a device configured to introduce an intended foreign substance into a target cell, using electrical action. The target cell is a cell that is the target for introducing the foreign substance. In the device 1, 10, an expensive pulse generator provided with a function to output a rectangular pulsed electric current in accordance with a program is not necessary. The device 1, 10 is configured to be able to significantly reduce use of a volume of a sample necessary for one processing cycle (a number of the target cells and an amount of the foreign substance).

As shown in FIG. 1 to FIG. 8, each of the devices 1, 10 is provided with a holding portion 2, a discharge generating portion 3, a conductive portion 4, a power amount control portion 5, and a power supply portion 6. The holding portion 2 holds a solution (a cell suspension, for example) containing the foreign substance and the cells. The solution is a liquid in which the foreign substance and the target cells are suspended in an aqueous solution. As the foreign substance, material that can be introduced into the target cells by existing electroporation is contained, and the foreign substance includes, for example, various types of biologically active substances that cannot pass through a cell membrane of the target cell in a normal state, drugs, therapeutic agents, nucleic acid substances, peptides, proteins, and the like. The nucleic acid substances may be, for example, DNA molecules, RNA molecules (including siRNA and guide RNA), virus DNA, plasmid DNA, oligonucleotides (antisense oligonucleotide, aptamer), and peptide nucleic acid. As the DNA, DNA provided with a nucleic acid sequence that is wished to be introduced into the target cell is selected as appropriate, and DNA designed in accordance with an objective is used, such as a full length sequence of a gene (a cDNA sequence, a genome sequence), a partial sequence, a control region, a spacer region, a sequence with an added mutation, and the like. A DNA encoded polypeptide can be produced by the target cell into which the DNA has been introduced. It is sufficient that an amount of the foreign substance contained in the solution be an amount with which known electroporation can be implemented. From the viewpoint of the probability of survival of the target cell and a transfer efficiency of the foreign substance, a concentration of the foreign substance in the cell suspension is preferably from 0.05 to 3 (μg/μL), is more preferably 0.2 to 3 (μg/μL), and is adjusted as appropriate depending on the foreign substance. The foreign substance contained in the solution is not limited to one type, and a plurality of types of foreign substance may be contained in the solution.

The type of the target cell is not particularly limited, and various types of cell can be used as the target cell. Examples of the target cell can include, for example, a plant cell, an animal cell including a human-derived cell, bacteria, and the like. The device 1, 10 can introduce the foreign substance into a cell into which the foreign substance can be introduced using a known electroporation method. Examples of the cell into which the foreign substance can be introduced using the known electroporation method include, for example, a human-derived and a non-human animal-derived somatic cell, an embryonic cell (ES cell), a fertilized egg, a tissue cell such as an animal embryonic tissue cell, an organ cell, and the like. With respect to a number of the cells required for processing, a number included in the solution to be held by the holding portion 2 is sufficient, and when a volume of the solution is 2 to 5 (μL), for example, it is sufficient that the number of target cells be $1\times10^3$ to $10^5$ (cells).

The solution is an aqueous solution, and is, for example, a buffer and a normal buffer solution that can be used in a normal electroporation method, such as phosphate buffered saline (hereinafter simply abbreviated to "PBS buffer solution"), a HEPES buffer solution (4-(2-hydroxyethyl)-1-piperazine ethanesulfonic acid), and the like. It is sufficient that the solution be adjusted as appropriate depending on the target cell. When the target cell is an animal cell, a liquid culture medium that can be used in the culture of animal cells (an MEM culture medium, a DMEM culture medium, an Opti-MEM culture medium, an α-MEM culture medium, an RPMI-1640 culture medium, a DMEM/F-12 culture medium, a Williams culture medium, an ES culture medium and the like, for example) can be used as the solution. With respect to these liquid culture media, compared to a case in which a serum concentration is high, a low serum concentration is favorable from the point of transfer efficiency, and in particular, a serum-free culture medium is preferable. In general, the solution is preferably a liquid culture medium that does not contain antibiotics. After processing by the device 1 to introduce the foreign substance, a serum or an antibiotic may be freely added to the liquid culture medium. From the viewpoint of transfer efficiency and an influence on the cell, the PBS buffer solution is preferably used as the solution. The pH of the solution is preferably adjusted taking into account an influence on the cell, and is preferably adjusted to a pH of 7.0 to 7.6.

The holding portion 2 may be provided with a pair of electrodes 21, 22 that are electrically connected to the discharge generating portion 3 via the conductive portion 4, and the holding portion 2 may be configured to hold the solution between the pair of electrodes 21, 22. The holding portion 2 may be provided with a container 23 and the pair of electrodes 21, 22 that are electrically connected to the discharge generating portion 3 via the conductive portion 4, and may be configured to hold the solution between the pair of electrodes 21, 22. The container 23 is formed of an insulating material, such as plastic, glass, ceramic, and the like, and contains the solution. It is sufficient that the shape of the holding portion 2 be a shape capable of holding the solution, and may be any shape. The container shape of the holding portion 2 may be, for example, a cylindrical shape, a square column shape, a polygonal column shape, a hemispherical shape, and the like. The size of the holding portion 2 is set depending on the volume of the solution to be held by the holding portion 2. The volume of the holding portion 2 is, for example, 0.3 to 50 times the volume of the solution, is preferably 0.5 to 20 times the volume of the solution, and is more preferably 0.8 to 10 times the volume of the solution. The volume of the solution is, for example, 0.1 (μL) to 1 (mL). The volume of the solution may be an amount able to form a droplet, and is selected, for example, from between 0.1 to 50 (μL), is preferably in a range from 0.5 to 10 (μL), and is more preferably in a range from 1.0 to 5.0 (μL). In a state in which the solution is held by the holding portion 2, an upper end of the container 23 is preferably set to be higher than an upper end of the solution. The pair of electrodes 21, 22 are preferably disposed so as to be able to be in contact with the solution, with a suitable gap therebetween, and the gap between the pair of electrodes 21, 22, for example, is selected between 0.2 to 10 (mm), preferably between 0.3 to 5.0 (mm), and more preferably between 0.5 to 2.0 (mm). The shape of the pair of electrodes 21, 22 may be set as appropriate, and may be, for example, a rod shape, a plate shape, and leading ends thereof may be a hemispherical shape, or the like. An arrangement of the pair of electrodes 21, 22 in relation to the container 23 may be set as appropriate, and each of the pair of electrodes 21, 22 may be disposed along a wall portion extending in a direction intersecting a bottom surface of the container 23. The pair of electrodes 21, 22 may be installed to extend from an opening to a bottom portion of the container 23, or the pair of electrodes 21, 22 may be separated from the bottom portion of the container 23. A thickness of the pair of electrodes 21, 22 may be set as appropriate, and is, for example, 0.1 to 10 (mm), is preferably selected from 0.2 to 5.0 (mm), or is more preferably selected from 0.5 to 2.0 (mm). It is sufficient that a material of the pair of electrodes 21, 22 be a material having conductive properties, and examples of the material can include, for example, metals having superior conductivity to carbon, such as aluminum, copper, and the like.

When there is a relatively small amount of the solution (1.0 (μL), for example), there is a possibility that the solution may evaporate when a pulsed electric current is applied to the solution held in the holding portion 2 by an arc discharge generated by the discharge generating portion 3. Taking this into account, in order to avoid evaporation of the solution, the holding portion 2 may be provided with an oil bath containing an oil for covering the solution, to separate the solution from the outside air. The oil bath is formed from an insulating material, and it is sufficient that the oil bath be configured to be able to retain the oil covering the solution. The oil stored in the oil bath phase-separates from water and is a substance that is more hydrophobic than the solution (water), is a liquid body in the vicinity of a normal temperature, and preferably has insulating properties. As the oil, for example, examples can include mineral oils, which are petroleum-derived alkanes, insulating oils whose main component is alkylbenzene, insulating oils whose main component is polybutene, insulating oils whose main component is alkylnaphthalene, insulating oils whose main component is alkyl diphenyl alkane, silicone oil, and the like. As the oil, one type of these oils may be used or a plurality of types may be mixed and used. As long as the oil has insulating properties, and is a hydrophobic liquid that does not mix with the solution, the oil is not limited to the examples above. The oil may be an insulating inert liquid, such as a fluorine-based inert liquid. In the present invention, the solution is held in the holding portion 2, and movement of the solution is regulated in a direction along the bottom portion of the container 23 (the horizontal direction). Thus, even when the holding portion 2 is provided with the oil bath, the solution held in the holding portion 2 is in the container 23, and the solution held in the holding portion 2 by the application of the voltage by the pair of electrodes 21, 22 does not move in the oil bath. From the viewpoint of deterioration due to usage, at least one selected from the group of the pair of electrodes 21, 22 and the container 23 may be provided in a replaceable manner.

The discharge generating portion 3 is configured to generate a pulsed electric current through arc discharge, and to supply the generated pulsed electric current to the holding portion 2 via the conductive portion 4. The discharge generating portion 3 includes a pair of electrodes 31, 32 disposed with a predetermined gap therebetween. The predetermined gap may be adjusted as appropriate while taking into account an installation environment of the discharge generating portion 3, and a magnitude, interval, frequency and the like of the pulsed electric current supplied to the holding portion 2. The predetermined gap is selected, for example, from 0.2 to 15 (mm), preferably from 0.3 to 5.0 (mm), and more preferably from 0.5 to 2.0 (mm). A thickness (width) of the pair of electrodes 31, 32 may be set as appropriate, and is, for example, 0.1 to 10 (mm), is preferably 0.2 to 5.0 (mm), or is more preferably selected from 0.5 to 2.0 (mm). The gap between the pair of electrodes 31, 32 may be changeable. When a distance between the pair of electrodes 31, 32 is changeable, at least one selected from the pair of electrodes 31, 32 may be slidable with respect to the other, or a plurality of electrodes having mutually different distances between the electrodes 31, 32 may be provided and one of the plurality of electrodes may be fixed in a removable manner, using a screw or the like. The shape of the electrodes 31, 32 may be set as appropriate, and leading ends thereof may have a curved shape, a spherical shape, a needle shape, or the like. It is sufficient that a material of the pair of electrodes 31, 32 be a material having superior conductivity to carbon, and examples of the material can include conductive metals, such as platinum, gold, aluminum, copper, and the like. Taking into account deterioration due to usage, the pair of electrodes 31, 32 may be provided in a replaceable manner.

Sometimes a dark current occurs between the pair of electrodes 31, 32 due to ion particles around the pair of electrodes 31, 32. Conditions under which the arc discharge occurs in the discharge generating portion 3 are easily affected by the dark current. Taking this into account, at least the pair of electrodes 31, 32 provided in the discharge generating portion 3 included in the device 1, 10 may be disposed in an inert gas, such as argon, for example.

The conductive portion 4 is electrically connected to the holding portion 2 and the discharge generating portion 3, and supplies the pulsed electric current generated by the discharge generating portion 3 to the holding portion 2. It is sufficient that the conductive portion 4 be formed of a material having conductive properties, and the conductive portion 4 is formed, for example, of a metal having superior conductivity to carbon, such as aluminum, copper, and the like. A width, length, shape and the like of the conductive portion 4 may be set as appropriate, and the length thereof is 5 to 500 times the predetermined gap between the pair of electrodes 31, 32 forming the discharge generating portion 3, for example. The conductive portion 4 may be integrally formed with the electrode 32 of the discharge generating portion 3 and the electrode 21 of the holding portion 2.

Figure 2:
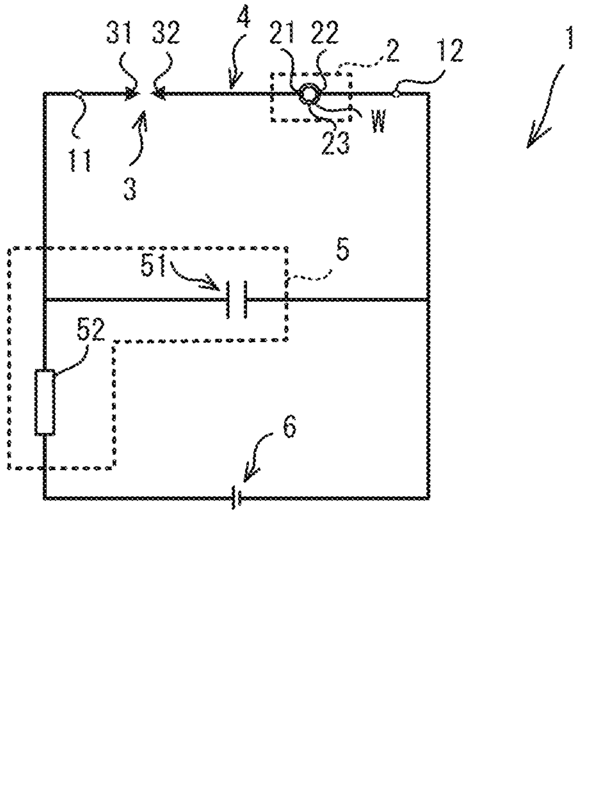
FIG. 2 is a diagram showing an example of a circuit of the electroporation device 1.
Figure 3:
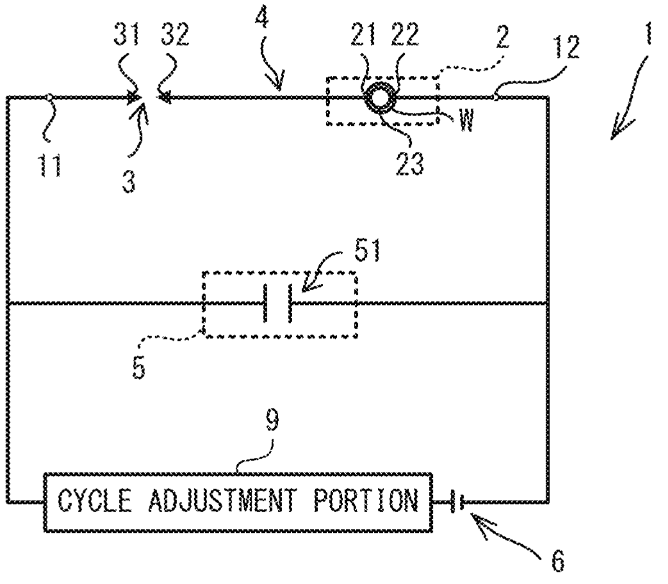
FIG. 3 is a diagram showing an example of a circuit of the electroporation device 1.
Figure 4:
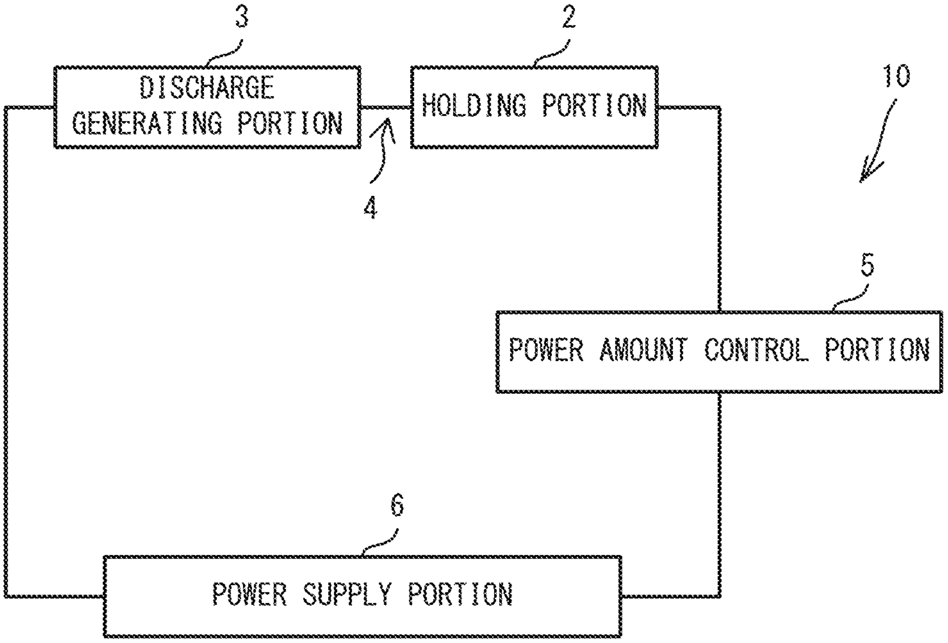
FIG. 4 is a conceptual diagram of an electroporation device 10.
Figure 5:
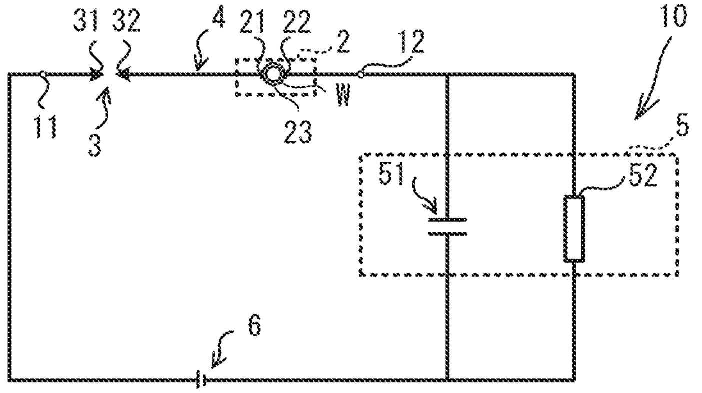
FIG. 5 is a diagram showing an example of a circuit of the electroporation device 10.

The power amount control portion 5 controls an amount of electric energy of the pulsed electric current supplied to the holding portion 2. The power amount control portion 5 is provided with a condenser 51. As shown in FIG. 2 and FIG. 3, the condenser 51 of the device 1 is electrically connected to the power supply portion 6 and the discharge generating portion 3, accumulates electricity as a result of voltage being applied by the power supply portion 6, and discharges the accumulated electric charge to the discharge generating portion 3. With respect to the power supply portion 6, the condenser 51 of the device 1 is connected in parallel with the discharge generating portion 3 and the holding portion 2. As shown in FIG. 5, the condenser 51 of the device 10 is electrically connected to the holding portion 2, and accumulates the pulsed electric current supplied to the holding portion 2. With respect to the power supply portion 6, the condenser 51 of the device 10 is connected in series with the discharge generating portion 3 and the holding portion 2. An electrostatic capacity of each of the condensers 51 of the device 1, 10 defines the amount of electric energy of the pulsed electric current supplied to the holding portion 2. Thus, the electrostatic capacity of the condenser 51 is set while taking into account the electrostatic capacity applied to the solution held by the holding portion 2. For example, the electrostatic capacity of the condenser 51 is set to 1.0 to 500 times the electrostatic capacity held by a droplet of 3 μL in silicone oil. Preferably the electrostatic capacity of the condenser 51 is set to 1.2 to 5.0 times the electrostatic capacity held by the droplet of 3 μL in silicone oil, and more preferably, is set to 2.5 to 3.5 times.

The electrostatic capacity applied to the solution held by the holding portion 2 can be calculated, for example, using Expression (1). When a volume V of the solution is 3.0 (μL) and the solution is a spherical shape with a radius r, an electrostatic capacity C of the solution can be calculated, using Expression (1) to be 7.76 (pF). Note that a dielectric constant $\varepsilon_0$ of a vacuum is assumed to be $8.854\times10^{-12}$ and a relative dielectric constant $\varepsilon_s$ of the solution is assumed to be 78.

$$\begin{aligned} C &= 4\pi\varepsilon_o\varepsilon_s r \\ &= 4\pi\varepsilon_0\varepsilon_s((3V/4\pi))^{1/3} \\ &= 4\times\pi\times8.854\times10^{-12}\times78\times \\ &\quad ((3\times3\times10^{-6}\times10^{-3})/4\pi)^{1/3} \\ &\approx 7.76\ (\text{pF}) \end{aligned} \qquad \text{Expression (1)}$$

When the volume V of the solution is 3.0 (μL), the electrostatic capacity of the condenser 51 is preferably set to 9.31 to 38.8 (pF), and is more preferably set to 19.4 to 27.2 (pF).

Figure 6:
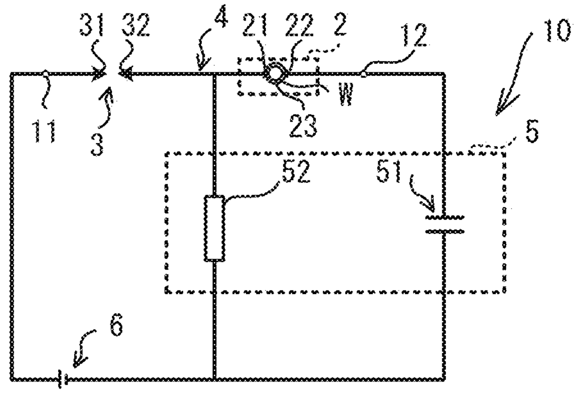
FIG. 6 is a diagram showing an example of a circuit of the electroporation device 10.

As shown in FIG. 2, FIG. 5, and FIG. 6, the power amount control portion 5 may be further provided with a dark current control portion 52. The dark current control portion 52 suppresses an influence of the dark current, by restricting the electric current supplied by the power supply portion 6 to only two currents, namely, the dark current generated between the pair of electrodes 31, 32 via a charged substance, such as ions or the like, in the air, and the electric current accumulated in the condenser 51 for supplying electricity to the holding portion 2. Further, the dark current control portion 52 can also control the electric current for charging the condenser 51. In order for a time period until completion of the accumulation of electricity in the condenser 51 to be proportional to the electric current supplied to the condenser 51, by controlling the electric current supplied to the condenser 51 using the dark current control portion 52, the device 1, 10 provided with the dark current control portion 52 can adjust an interval of the arc discharge generated by the pair of electrodes 31, 32. The dark current control portion 52 of the device 1 shown in FIG. 2 is provided between the power supply portion 6 and the discharge generating portion 3. On the other hand, the dark current control portion 52 of the device 10 shown in FIG. 5 is connected in parallel with the condenser 51 with respect to the holding portion 2. The dark current control portion 52 of the device 10 shown in FIG. 6 is connected in parallel with the condenser 51 with respect to the discharge generating portion 3.

The dark current control portion 52 is a known electric resistance, for example. A magnitude of an electric resistance R can be calculated from Expression (2). Note that, a magnitude of the voltage applied by the power supply portion 6 is E, the electrostatic capacity of the condenser 51 is C, and a magnitude of the dark current is $I_d$.

$$R=E/(C\times dV/dt+I_d) \qquad \text{Expression (2)}$$

Taking into account consideration of an electric resistance value optimal for generating the arc discharge by the discharge generating portion 3, the dark current control portion 52 may be provided with a variable resistor.

Figure 7:
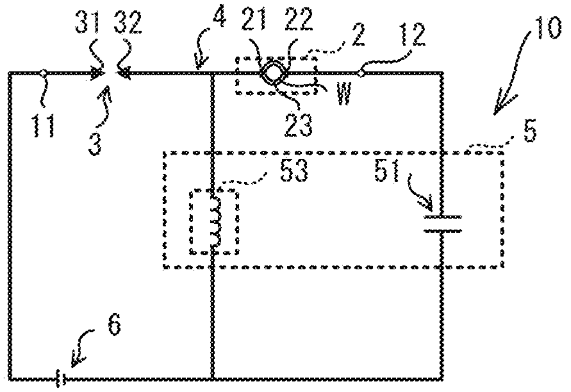
FIG. 7 is a diagram showing an example of a circuit of the electroporation device 10.

As shown in FIG. 7, in the power amount control portion 5, an inductor (coil) 53 for applying a counter electromotive force to the discharge generating portion 3 may be connected in parallel with the holding portion 2 and the condenser 51. Before the discharge occurs in the discharge generating portion 3, the electric current flowing through the inductor 53 is, in theory, only the electric current corresponding to the dark current. When the voltage between the pair of electrodes in the discharge generating portion 3 exceeds a dielectric breakdown voltage of the air in a distance (1 (mm), for example) between the pair of electrodes of the discharge generating portion 3, the discharge occurs between the pair of electrodes of the discharge generating portion 3, and the pair of electrodes of the discharge generating portion 3 conduct electricity. The inductor 53 attempts to maintain the electric current to be constant (Lenz's law), and thus, when a sudden current change occurs in the discharge generating portion 3, the inductor 53 acts such that the electric current does not flow through the inductor 53. Thus, the electric current does not flow through the inductor 53 immediately after the discharge has occurred in the discharge generating portion 3, and an electric charge is charged to the condenser 51 via the holding portion 2. When the electric charge is accumulated in the condenser 51, an end-to-end voltage of the condenser 51 (a difference in potential between two wires connected to the condenser 51) is higher than when the electric charge is not accumulated in the condenser 51. As a result, of the wires connected to the condenser 51, a difference between the potential of the wire connected to the holding portion 2 and a potential on the positive side of a DC power supply device becomes small, and the discharge of the discharge generating portion 3 stops. The inductor 53 has a characteristic to prevent the current changes, but since the electric current starts flowing through the inductor 53 when a constant time period (an inductance time constant) elapses, when the discharge in the discharge generating portion 3 stops, the accumulated electric charge in the condenser 51 is discharged through the inductor 53. The orientation of the electric current at this time is a reverse orientation to the voltage applied by the supply from the power supply device, and thus, the voltage applied to the holding portion 2 becomes the reverse direction. When the electric charge accumulated in the condenser 51 is discharged, a potential of a wire between the discharge generating portion 3 and the holding portion 2 decreases, and thus, the voltage between the pair of electrodes of the discharge generating portion 3 once more increases.

An inductance value of the inductor 53 may be set while taking into account both obstructing the electric current from flowing through the inductor 53 until the electric charge corresponding to the electrostatic capacity accumulates in the condenser 51, and allowing the electric current to flow through the inductor 53 after the electric charge corresponding to the electrostatic capacity has accumulated in the condenser 51. In other words, the inductance value of the inductor 53 is set to an inductance value at which the charging and the discharge of the condenser 51 is possible. The electromotive force generated in the inductor 53 is expressed by the product of the current change and the inductance value. In other words, the electromotive force generated in the coil is expressed using Expression (3).

Electromotive force generated in coil=inductance value×(magnitude of current change/time required for electric current change) Expression (3)

It is possible that the energy of the pulsed electric current applied in order to introduce the foreign substance, such as a gene, into the target cell in the solution can be adjusted using the inductance value of the inductor 53 of the device 10.

Figure 8:
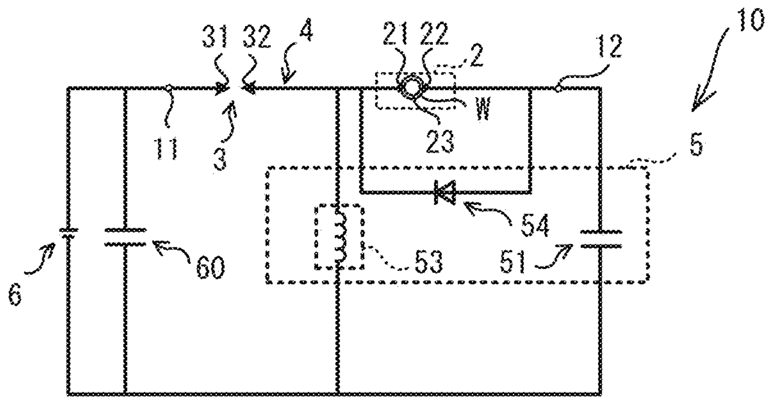
FIG. 8 is a diagram showing an example of a circuit of the electroporation device 10.

As shown in FIG. 8, in the power amount control portion 5, with respect to the discharge generating portion 3, the inductor 53 may be provided in parallel with the holding portion 2 and the condenser 51, and a diode 54 may be provided in parallel with the holding portion 2. A forward direction of the diode 54 is the direction in which the electric current discharged from the condenser 51 flows. The type of the diode 54 may be set as appropriate. A diode suited to high-speed switching and high frequency rectification is preferably used, and a Schottky barrier diode is used as the diode 54, for example. While, in the device 10 shown in FIG. 7 that is not provided with the diode 54, a waveform of the pulsed electric current that is applied to the holding portion 2 indicates an attenuated vibration waveform, in the device 10 shown in FIG. 8 that is provided with the diode 54, a waveform of the pulsed electric current that is applied to the holding portion 2 becomes a waveform in which, due to the action of the diode 54, a negative component (a current component flowing from the condenser 51 in the direction of the inductor 53) in the attenuated vibration waveform pulsed electric current is eliminated.

The power supply portion 6 is configured to apply the voltage to the discharge generating portion 3. It is sufficient that the power supply portion 6 be able to apply the voltage capable of causing the discharge generating portion 3 to generate the arc discharge, and is, for example, a DC high-voltage power supply of 3 kV or more. A maximum output voltage of the power supply portion 6 is 5 kV or more, for example, and a maximum output current of the power supply portion 6 is 1.0 mA or more. Although not shown in the drawings, the power supply portion 6 may be provided with a switch for switching the voltage application on and off, a dial for adjusting the voltage to be supplied, and a timer for setting a desired time period. In this case, the device 1 may be configured such that when the voltage to be supplied is set by an operator using the dial, and the desired time period is set on the timer, the voltage application starts when the switch is turned on, and the switch is turned off when the time period set on the timer ends thus stopping the voltage application. In each of the devices 1, 10, as a configuration for applying a high-voltage DC to the discharge generating portion 3, a known inverter circuit (a cold cathode fluorescent lamp inverter (CCFL circuit) for example), a high-voltage generating circuit (a Cockcroft-Walton circuit (CCW circuit) for example) and the like may be combined as appropriate and used. As shown in FIG. 8, in the power supply portion 6, a condenser 60 may be provided in series with the discharge generating portion 3 and the holding portion 2. In such a case, the power supply portion 6 can change a discharge cycle of the discharge generating portion 3 using a value of the condenser 60.

Conditions of the voltage applied to the discharge generating portion 3 from the power supply portion 6 may be adjusted as appropriate. For example, the device 1 may be further provided with a cycle adjustment portion 9 for applying the voltage to the discharge generating portion 3 in a cyclical manner at a predetermined interval, as in the device 1 exemplified in FIG. 3, and may apply the voltage to the discharge generating portion 3 at a predetermined cycle. The predetermined cycle may be set as appropriate, and an ON period may be set to be shorter than an OFF period, at a cycle of 150 to 300 (ms), for example, and the ON period may be set to be approximately 1/30 to 1/3 of the OFF period. A number of times that the voltage is applied to the discharge generating portion 3 at the predetermined cycle corresponds to a number of times that the pulsed electric current is generated by the arc discharge by the discharge generating portion 3. The number of times that the pulsed electric current is generated in the discharge generating portion 3 is set as appropriate while taking into account both the transfer efficiency of the foreign substance, and the probability of survival of the target cell. The number of times that the pulsed electric current is generated in the discharge generating portion 3 is, for example, 1 to 500 times, is preferably 3 to 200 times, and is more preferably 5 to 100 times.

2. Method for Producing Cells with Introduced Foreign Substance Using Device 1

Figure 34:
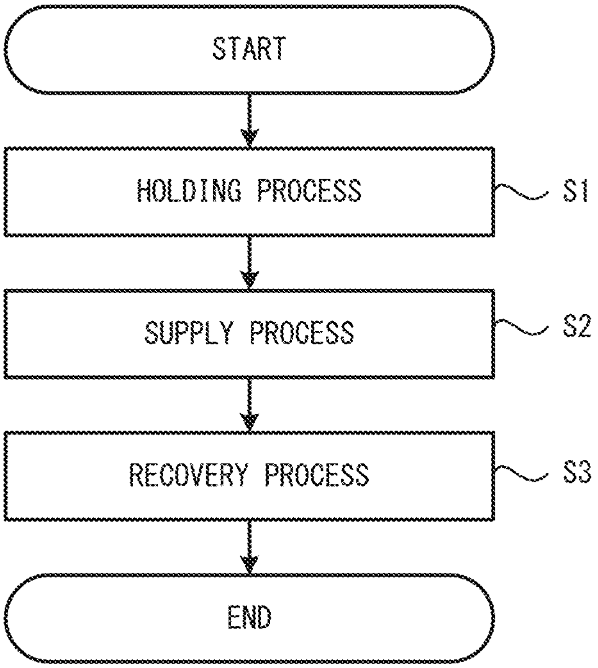
FIG. 34 is a flowchart of processes for producing cells with an introduced foreign substance.

As shown in FIG. 34, the operator causes the foreign substance and the solution containing the cell to be held in the holding portion 2 (holding process, S1). When the high-voltage DC is applied to the power amount control portion 5 by the power supply portion 6, the electric charge accumulates in the condenser 51. Until the voltage of the condenser 51 reaches a predetermined voltage, electric current does not flow through the pair of electrodes 31, 32 of the discharge generating portion 3. When the voltage of the condenser 51 reaches the predetermined voltage, the electric charge accumulated in the condenser 51 is discharged to the discharge generating portion 3, and causes the discharge generating portion 3 to generate the arc discharge. The pulsed electric current generated by the arc discharge is supplied to the holding portion 2 via the conductive portion 4 (supply process, S2). The pulsed electric current supplied to the holding portion 2 flows between the pair of electrodes 21, 22 of the holding portion 2. When the arc discharge has been generated by the discharge generating portion 3 a predetermined number of times, the processing ends. The operator recovers the solution held in the holding portion 2 (recovery process, S3).

3. Method for Producing Cells with Introduced Foreign Substance Using Device 10

As shown in FIG. 34, the operator causes the foreign substance and the solution containing the cell to be held in the holding portion 2 (holding process, S1). When the difference in potential between both ends of the condenser 51 is smaller than a predetermined value, when the high-voltage DC is applied to the discharge generating portion 3 by the power supply portion 6, the arc discharge is generated in the discharge generating portion 3. The pulsed electric current generated by the arc discharge is supplied to the holding portion 2 via the conductive portion 4 (supply process, S2). The pulsed electric current supplied to the holding portion 2 flows between the pair of electrodes 21, 22 of the holding portion 2. The condenser 51 of the power amount control portion 5 accumulates the pulsed electric current supplied to the holding portion 2. When the electric charge accumulated in the condenser 51 reaches the electrostatic capacity of the condenser 51, the difference in potential between both ends of the condenser 51 becomes equivalent to the supply voltage of the power supply portion 6, and the arc discharge in the discharge generating portion 3 stops. Thus, the amount of electric charge that can flow via the holding portion 2 is only the amount of electric charge that can be accumulated in the condenser 51 connected in series to the holding portion 2. When the arc discharge by the discharge generating portion 3 stops, the electric charge accumulated in the condenser 51 is discharged through the dark current control portion 52 of the power amount control portion 5, the difference in potential between both ends of the condenser 51 decreases, and the difference in potential between the pair of electrodes 31, 32 of the discharge generating portion 3 increases. When the difference in potential between the pair of electrodes 31, 32 of the discharge generating portion 3 once more becomes larger than a predetermined value, the arc discharge is generated. As shown in FIG. 7 and FIG. 8, when the device 10 is provided with the inductor 53, the inductor 53 connected in parallel with the holding portion 2 and the condenser 51 discharges the electric charge accumulated in the condenser 51. Since, for a time of discharge by the inductor 53 also, the electric current flowing via the holding portion 2 (the amount of electric charge passing through the solution held by the holding portion 2) is only the amount of electric charge accumulated in the condenser 51, the power amount control is also applied at the time of discharge. When the arc discharge is generated by the discharge generating portion 3 the predetermined number of times, the processing ends. The operator recovers the solution held in the holding portion 2 (recovery process, S3).

In the method of producing the cells with the introduced foreign substance using the device 1, 10, an intense pulsed electric field is conceivably formed in an instant at which the arc discharge is generated by the discharge generating portion 3, in a droplet W disposed between the pair of electrodes of the holding portion 2. Due to the action of the intense electric field formed in the droplet W, it is presumed that micropores are temporarily formed in a cell membrane of the target cell, and the foreign substance is introduced into the target cell from the formed pores. Compared to an ON period of the pulsed electric current generated by a known pulse generator, a time period in which the pulsed electric current generated by the arc discharge flows in the holding portion 2 is sufficiently short. More specifically, the device 1, 10 can generate the pulsed electric current having a short application time period that is almost impossible to generate in the known pulse generator. Thus, the amount of electric energy applied to the target cell in the solution held in the holding portion 2 is small compared to that of the known electroporation device, and damage imparted to the target cell is conceivably reduced.

4. Example 1

Figure 9:
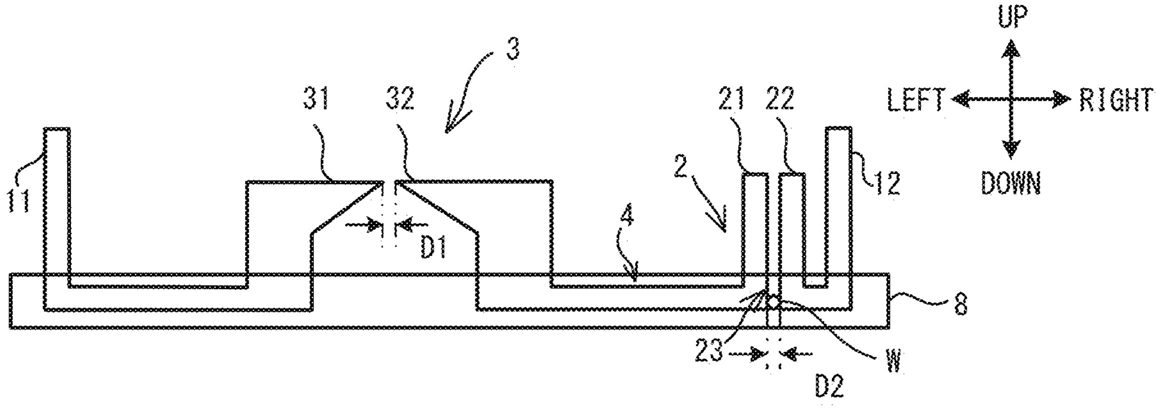
FIG. 9 is a schematic diagram of a holding portion 2, a discharge generating portion 3, and a conductive portion 4 of the electroporation device 1 according to Example 1.
Figure 10:
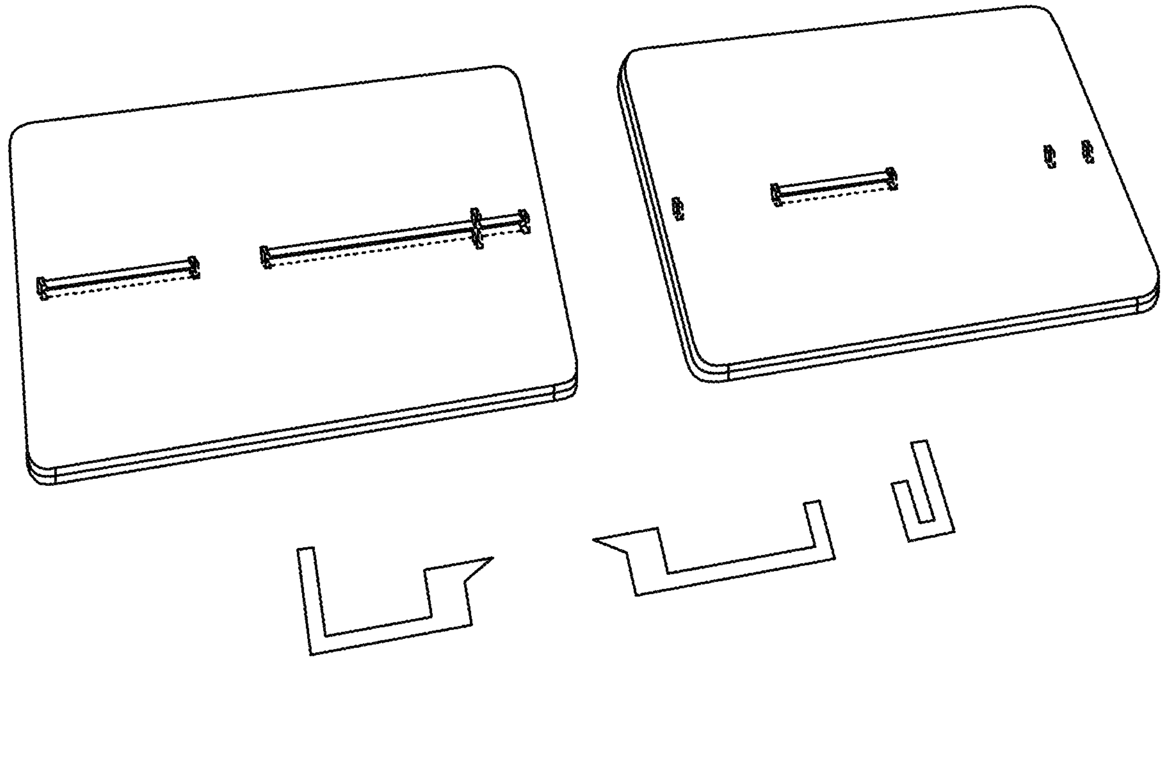
FIG. 10 is a photograph of the holding portion 2, the discharge generating portion 3, and the conductive portion 4 of the electroporation device 1 according to Example 1 before assembly.
Figure 11:
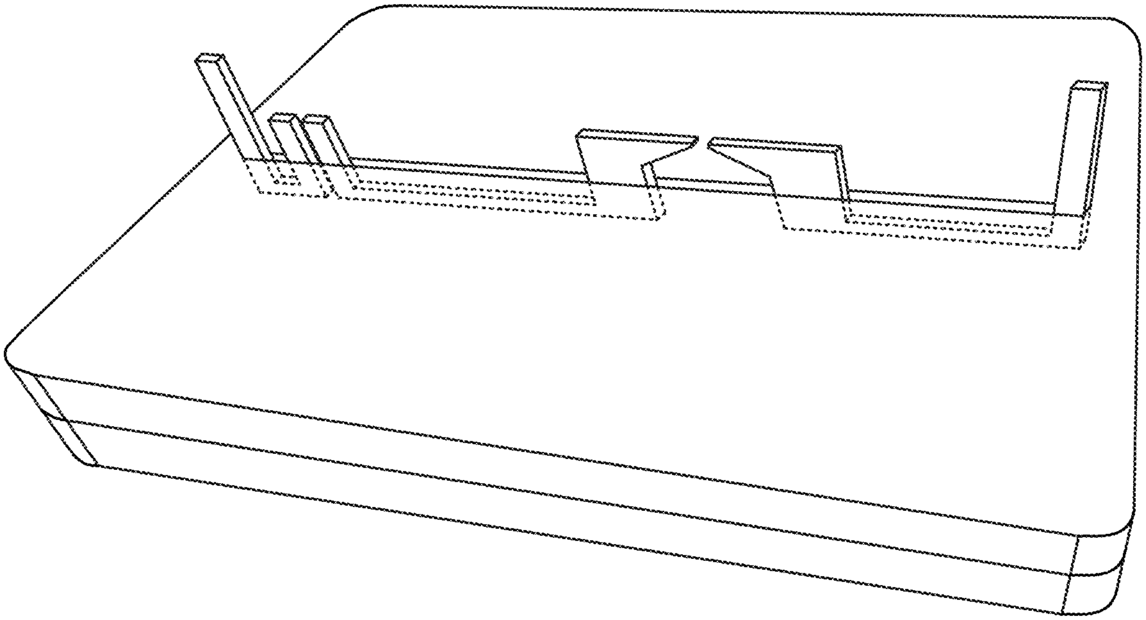
FIG. 11 is a photograph of the holding portion 2 and the discharge generating portion 3 of the electroporation device 1 according to Example 1 after assembly.
Figure 12:
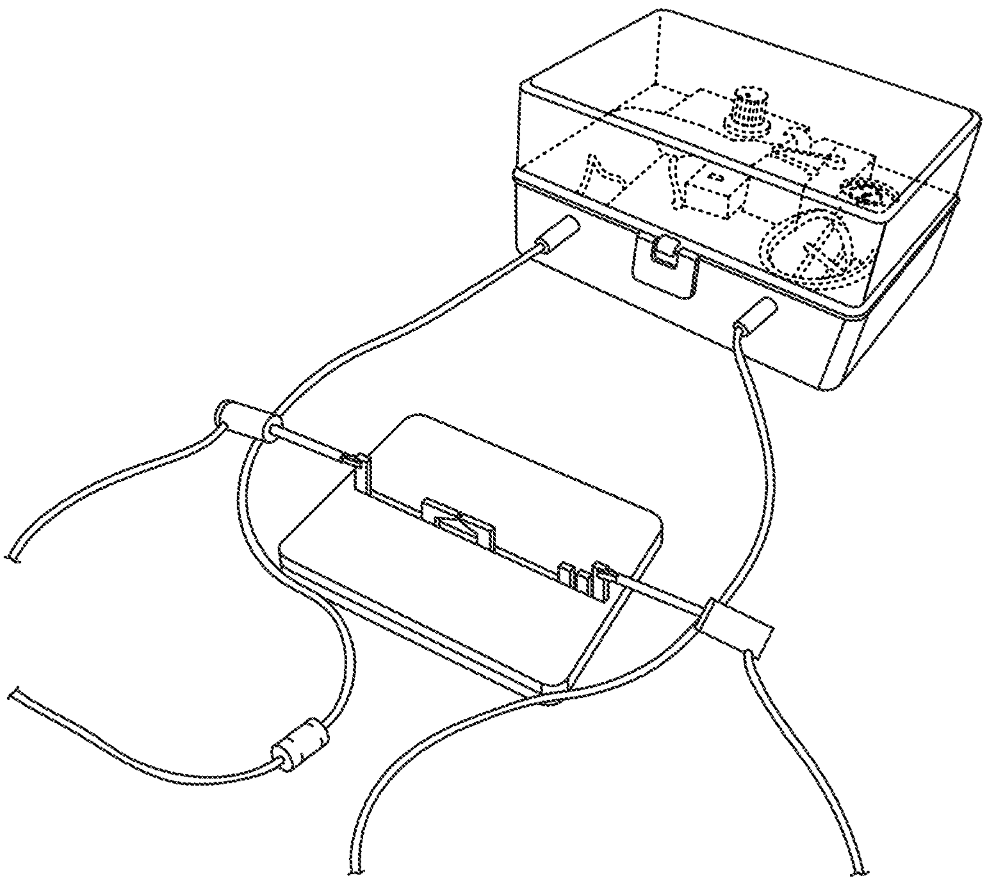
FIG. 12 is a photograph of the electroporation device 1 according to Example 1 after assembly.

The device 1 shown in FIG. 2 and FIG. 9 to FIG. 12 was manufactured, and cells with an introduced foreign substance were produced using the manufactured device 1. As shown in FIG. 2, the device 1 according to Example 1 is provided with the holding portion 2, the discharge generating portion 3, the conductive portion 4, the power amount control portion 5, and the power supply portion 6. The holding portion 2 is provided with the pair of electrodes 21, 22, and the container 23. The discharge generating portion 3 is provided with the pair of electrodes 31, 32. As shown in FIG. 9, the pair of electrodes 21, 22, the conductive portion 4, and the pair of electrodes 31, 32 were processed and manufactured of an aluminum plate (A1000 series, pure aluminum based) having a thickness of 1.0 (mm). The pair of electrodes 21, 22 were formed in a rectangular shape extending in the vertical direction. The pair of electrodes 31, 32 were formed in a triangular shape narrowing toward end portions thereof, with side surface shapes thereof facing each other. As shown in FIG. 10, slits extending in the vertical direction were formed in an insulating resin plate (acrylic plate) 8, in accordance with the shape and arrangement of the pair of electrodes 21, 22 and of the pair of electrodes 31, 32. As shown in FIG. 11, the pair of electrodes 21, 22 and the pair of electrodes 31, 32 were disposed in the formed slits. The pair of electrodes 21, 22 disposed in the slits extended in the vertical direction and were disposed with a gap D2 of 1.6 (mm) therebetween. The pair of electrodes 31, 32 extended in the vertical direction and were disposed with a gap D1 of 1.0 (mm) therebetween. The power amount control portion 5 is provided with the condenser 51 and the dark current control portion 52. The electrostatic capacity of the condenser 51 was 22 (pF), and the electric resistance of the dark current control portion 52 was 45 (MΩ). As the power supply portion 6, a high-voltage DC power supply of 3 kV or more was used. As shown in FIG. 12, taking safety into account, the condenser 51, the dark current control portion 52, and the power supply portion 6, which are high-voltage generating components, were housed in a plastic case. The components housed in the plastic case were electrically connected, using conductive clips, to an end portion 11 of the electrode 31 and an end portion 12 of the electrode 22. Overall, the length, width, and height of the device 1 were approximately 10 (cm), 10 (cm), and 10 (cm), and the device 1 could be placed on the palm of a hand.

With respect to the solution (the cell suspension), the target cells were HEK293 cells, the foreign substance was the fluorescent protein fused Luciferase: the fortissimo luciferase (ffLuc) gene, and the aqueous solution was the medium culture OPTI-MEM or the PBS buffer solution. The ffLuc gene is a gene in which a recombination sequence is formed using gene recombination technology to couple, downstream of a promoter region of the cytomegalovirus (CMV), fusion protein encoding genes formed of yellow fluorescent protein Venus (derived from *Aequorea victoria*) and photoprotein luciferase (derived from fireflies) and the recombination sequence is held on plasmid DNA. By introducing this recombinant gene into the target cell through gene transfection, the target cell emits a fluorescence signal.

The HEK293 cells were spread in a plastic culture vessel (culture dish) having a diameter of 10 (cm), with a cell density of $5\times10^5$ (cell/dish), and were cultured in an incubator, using a high glucose DMEM culture medium at a temperature of 37 degrees Celsius, and with a $CO_2$ concentration of 5%. The cultured HEK293 cells were removed from the culture dish by trypsinization, and a cell suspension was prepared with the aqueous solution being the culture medium OPTI-MEM or the PBS buffer solution in which a HEK293 cell density was $5\times10^3$ (cell/μL), and an HEK293 expressed plasmid DNA density was 112 (ng/μL). The 3 (μL) droplet W was formed using the prepared cell suspension, and fed into the container 23 surrounded by the pair of electrodes 21, 22 of the device 10 and the insulating resin plate 8. A condition (Condition 1) was set in which the droplet W held in the holding portion 2 was sealed from the outside using silicone oil of 20 (cSt), and conditions (Conditions 2, 3) were set in which the droplet W held in the holding portion 2 was not sealed using the silicone oil.

The time period over which the voltage was applied to the discharge generating portion 3 directly connected to the holding portion 2 was set to 15 seconds or 30 seconds. Specifically, the voltage was applied to the discharge generating portion 3 for 30 seconds under Condition 1, for 15 seconds under Condition 2, and for 30 seconds under Condition 3. When the voltage is applied to the discharge generating portion 3, theoretically the arc discharge is generated at 3 kV. During the period in which the voltage was applied to the discharge generating portion 3 by the power supply portion 6, an arc discharge of a high voltage and of a short period (several microseconds) was generated intermittently. As a negative control, samples under a condition in which the voltage was not applied to the holding portion 2 were prepared in a similar manner.

Figure 13:
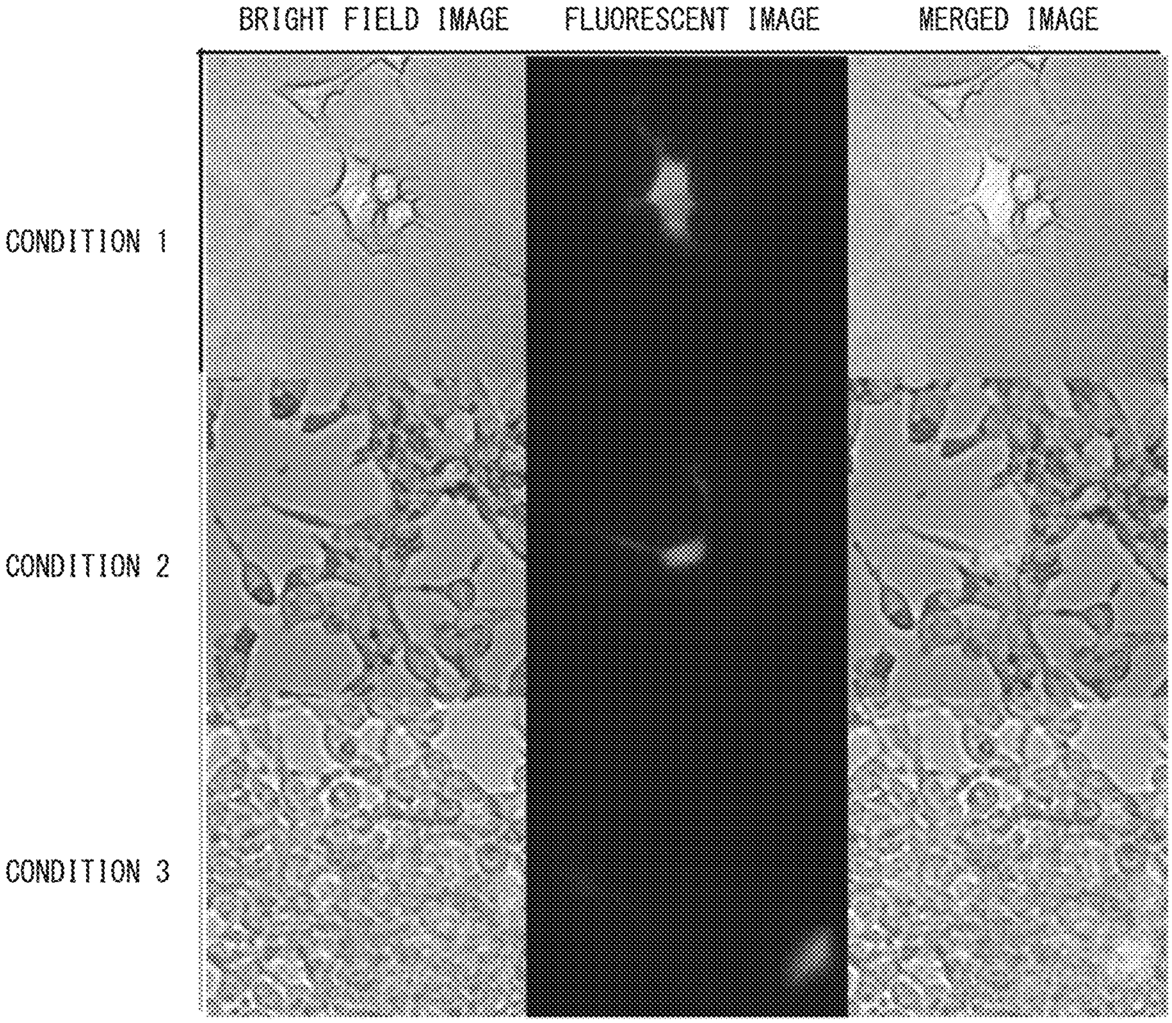
FIG. 13 includes observation images seven days after a fluorescent protein encoding gene has been introduced, under Conditions 1 to 3, using the electroporation device 1 according to Example 1, and is a diagram showing microscope observation images in a bright field (20× magnification objective lens as the observation magnification), fluorescent images in a fluorescent light field (20× observation magnification), and superimposed images obtained by superimposing the bright field images and the fluorescent field images.

After the voltage was applied to the holding portion 2, the solution held in the holding portion 2 was recovered. The recovered solution was added to a 6 to 24 well plastic bottom plate into which a prepared culture medium had been injected, and the target cells were cultured in the solution under the conditions of 37° C., and the $CO_2$ concentration of 5%. The target cells were observed, using a fluorescence microscope, after 2 to 7 days from the start of the culture. The target cells were excited using a 490 nm LED as a light source, and fluorescence signals in the vicinity of 510 nm were measured with the fluorescence microscope using a 20× magnification objective lens. As shown in FIG. 13, the cells having the fluorescence signals were observed under each of Conditions 1 to 3, and it was confirmed that introduction of the fusion protein encoding gene into the target cells was successful by the method using the device 1. Although not shown in FIG. 13, in the cells under the negative control, the fluorescence signals by the fusion protein encoding genes were not confirmed.

The cells used in the fluorescence imaging were collected and a number of the cells emitting the fluorescence signals were measured using an image sight meter (Tali, manufactured by Thermo Fisher Scientific). As a threshold value for the fluorescence signals, a value obtained by adding a value of twice a standard deviation to an average value of a background signal (Mean+2SD) was used. The background signal was a self-fluorescence signal under the negative control. A ratio of the cells having the fluorescence signals of the above-described threshold value or above, with respect to a total number of the cells, was calculated as a transfection efficiency. The transfection efficiency under Condition 2 was 17.67%, and the transfection efficiency under Condition 3 was 12.42%.

As described above, according to the device 1, it was confirmed that the foreign substance could be introduced into the target cell at a favorable introduction efficiency, using the electric action. Since the device 1 uses the electric action, a special reagent is not needed, and, compared to a chemical method, running costs can be suppressed. Further, the device 1 can obtain the cells with the introduced foreign substance with a favorable probability of survival, without fear of oncogenesis caused by toxicity and antigenicity to the target cells, as occurs in a biological approach using a virus. The device 1 does not require the expensive pulse generator that is provided with the function to output the rectangular pulsed electric current in accordance with the program, which is indispensable in the general electroporation device. Since the configuration of the device 1 is simple, the device 1 is manufactured at low cost. In the device 1, it is not necessary to use oil, and the device 1 can thus also be applied to samples for which it is preferable not to use the oil.

5. Example 2

Figure 14:
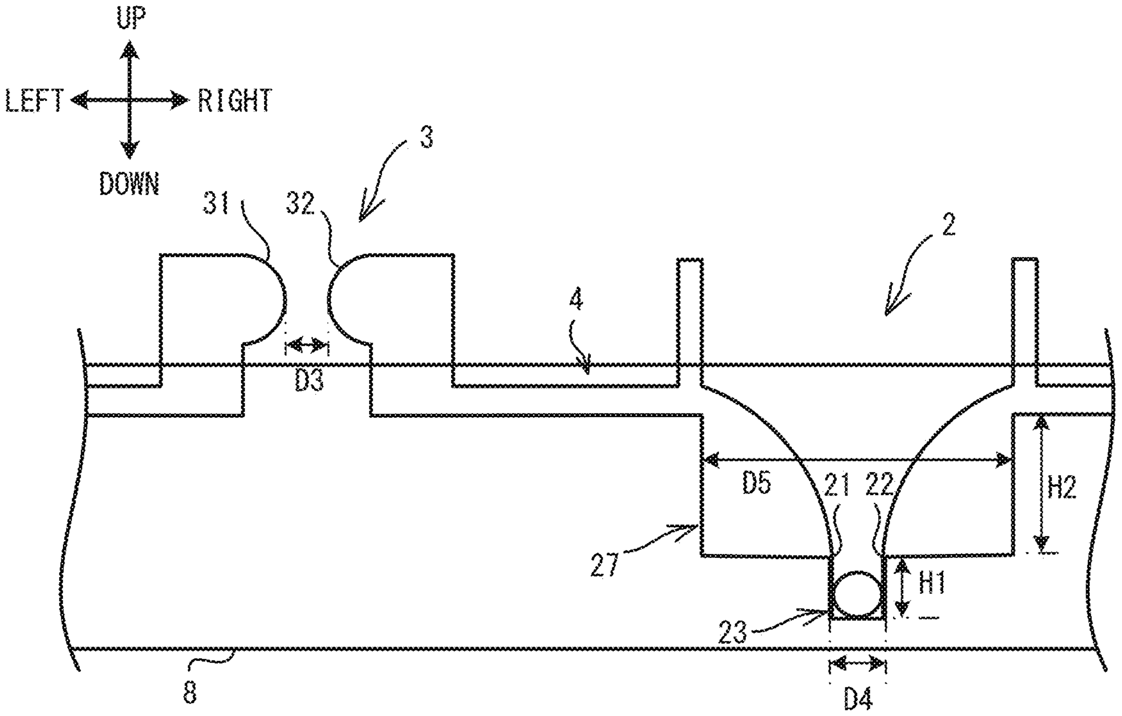
FIG. 14 is a schematic diagram of the holding portion 2, the discharge generating portion 3, and the conductive portion 4 of the electroporation device 1 according to Example 2.
Figure 15:
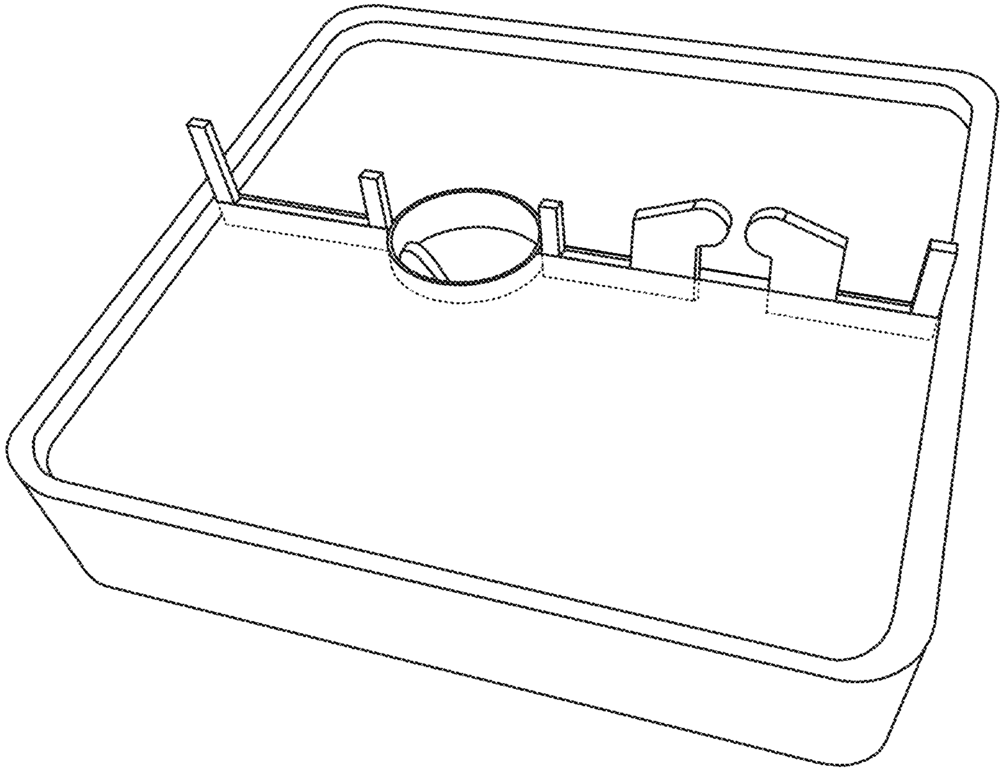
FIG. 15 is a photograph of the holding portion 2 and the discharge generating portion 3 of the electroporation device 1 according to Example 2 after assembly.

The device 1 of Example 1 is a device in which the dielectric breakdown voltage is designed using a parallel plate of an unlimited area. Thus, it is conceivable that the dielectric breakdown voltage in the pair of electrodes 31, 32 each having the shape with a pointed leading end may become smaller than an estimated voltage. Here, in Example 2, as shown in FIG. 3, FIG. 14, and FIG. 15, the device 1 was manufactured in which the leading end shape of the pair of electrodes 31, 32 of the discharge generating portion 3 was designed to be hemispherical, and the cells with the introduced foreign substance were produced using the manufactured device 1. The device 1 according to Example 2 is provided with the holding portion 2, the discharge generating portion 3, the conductive portion 4, the power amount control portion 5, and the power supply portion 6. As shown in FIG. 14 and FIG. 15, the holding portion 2 is provided with the pair of electrodes 21, 22, the container 23, and an oil bath 27. The discharge generating portion 3 is provided with the pair of electrodes 31, 32. The pair of electrodes 21, 22, the conductive portion 4, and the pair of electrodes 31, 32 were processed and manufactured of an aluminum plate (A1000 series, pure aluminum based) having a thickness of 1.0 (mm).

By processing the insulating resin plate (acrylic plate) 8, the container 23 was formed in a cylindrical shape having a diameter D4 of 1.6 (mm), and a depth H1 of 2.0 (mm). The oil bath 27 was formed in a cylindrical shape having a diameter D5 of 10 to 12 (mm), and a depth H2 of 6 to 10 (mm), with an upper end of the container 23 being the height of a bottom surface of the oil bath 27. The container 23 was provided substantially in the center of the bottom portion of the oil bath 27. Sections, of the pair of electrodes 21, 22, housed in the container 23 extended in the vertical direction and sections thereof housed in the oil bath 27 were formed in an arc shape such that the pair of electrodes 21, 22 moved apart from each other the further they were separated from the container 23 in the up-down direction (the further they were toward the upper side). The pair of electrodes 31, 32 were formed in a hemispherical shape such that surfaces on the sides of the pair of electrodes 31, 32 facing each other formed protrusions. Slits were formed in the insulating resin plate 8 having a thickness of 10 (mm), in accordance with the arrangement, and shape of the pair of electrodes 21, 22 and of the pair of electrodes 31, 32. As shown in FIG. 15, the pair of electrodes 21, 22 and the pair of electrodes 31, 32 were disposed in the formed slits. The pair of electrodes 21, 22 extended in the vertical direction and were disposed with a gap D4 of 1.0 (mm) therebetween. The pair of electrodes 31, 32 extended in the vertical direction and were disposed with a gap D3 of 1.0 (mm) therebetween. The power amount control portion 5 is provided with the condenser 51. The electrostatic capacity of the condenser 51 was 200 (pF). In a similar manner to the device 1 according to Example 1, taking safety into account, the condenser 51, which is the high-voltage generating component, was housed in a plastic case. The component housed in the plastic case was electrically connected, using conductive clips, to the end portion 11 of the electrode 31 and the end portion 12 of the electrode 22.

The device 1 according to Example 2 further includes the cycle adjustment portion 9 for creating an interval period over which the voltage is applied to the discharge generating portion 3. The cycle adjustment portion 9 includes a control system (Arduino (Registered trademark)). In the cycle adjustment portion 9, a cycle was set to 200 (ms), and two conditions were set as the interval, namely, 190 (ms) (Condition 4), and 180 (ms) (Condition 5).

With respect to the solution (the cell suspension), the target cells were HEK293 cells, the foreign substance was the pCXLE-EGFP gene, and the aqueous solution was the culture medium OPTI-MEM buffer. The pCXLE-EGFP gene is a gene in which a recombination sequence is formed using gene recombination technology to couple a green fluorescent protein EGFP encoding gene downstream of a promoter region of CMV (cytomegalovirus). By introducing this recombinant gene into the target cell through gene transfection, the target cell emits a fluorescence signal.

The HEK293 cells were spread in a plastic culture dish having a diameter of 10 (cm), with a cell density of $5\times10^4$ (cell/dish), and were cultured in an incubator, using a high glucose DMEM culture medium at a temperature of 37 degrees Celsius, and with a $CO_2$ concentration of 5%.

The cultured HEK293 cells were removed from the culture dish by trypsinization, and a cell suspension was prepared under conditions in which a HEK293 cell density was $1\times10^4$ (cell/μL), a pCXLE-EGFP plasmid DNA density was 100 (ng/μL), and the aqueous solution was the culture medium OPTI-MEM. The 4 (μL) droplet W of the prepared cell suspension was introduced into the container 23 in the device 1. Both Condition 4 and Condition 5 were conditions in which the droplet W held in the holding portion 2 was not sealed by the oil, such as silicone oil.

The voltage was applied 10 times to the discharge generating portion 3 electrically connected to the holding portion 2 via the conductive portion 4 at the cycles of the above-described Conditions 4 and 5. As a negative control, the cell suspension was prepared to which the voltage was not applied. As a positive control, cells were prepared into which the pCXLE-EGFP gene was transduced using the lipofection method using lipofectamine 3000 (Invitrogen) as a liposome.

Figure 16:
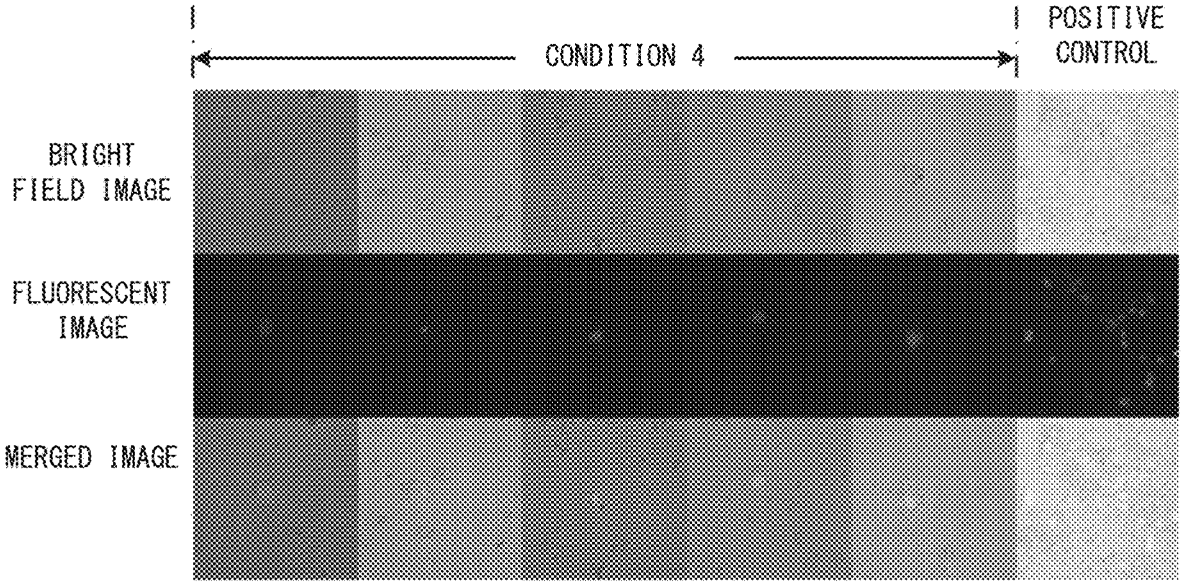
FIG. 16 is a diagram showing a fluorescent observation result on a day after a transfection operation of the target cell (Condition 4) on which a gene transfection operation has been performed using the electroporation device 1 according to Example 2, and a fluorescent observation result of a target cell (a positive control) on which the gene transfection operation has been performed by lipofection method using a Lipofectamine 3000 reagent.

For the samples processed under each of the conditions, after culturing the cells under conditions of 37 degrees Celsius and 5% $CO_2$, the cells were excited using a 490 nm LED as a light source, and fluorescence signals in the vicinity of 510 nm were measured with a fluorescence microscope using a 20× magnification objective lens. In the negative control, no fluorescence signals were detected from the target cells due to expression of the fluorescent protein from the target cells, and, as shown in FIG. 16, in the positive control, the fluorescence signals were detected from the target cells due to expression of the fluorescent protein. Under Condition 5, the expression of the fluorescent protein was not confirmed, but, as shown in FIG. 16, under Condition 4, in comparison to the positive control, although the transfection efficiency is low, the expression of the fluorescent protein was confirmed. In the device 10 also, it is conceivable that the same effects as those of the device 1 can be obtained.

6. Example 3

Figure 19:
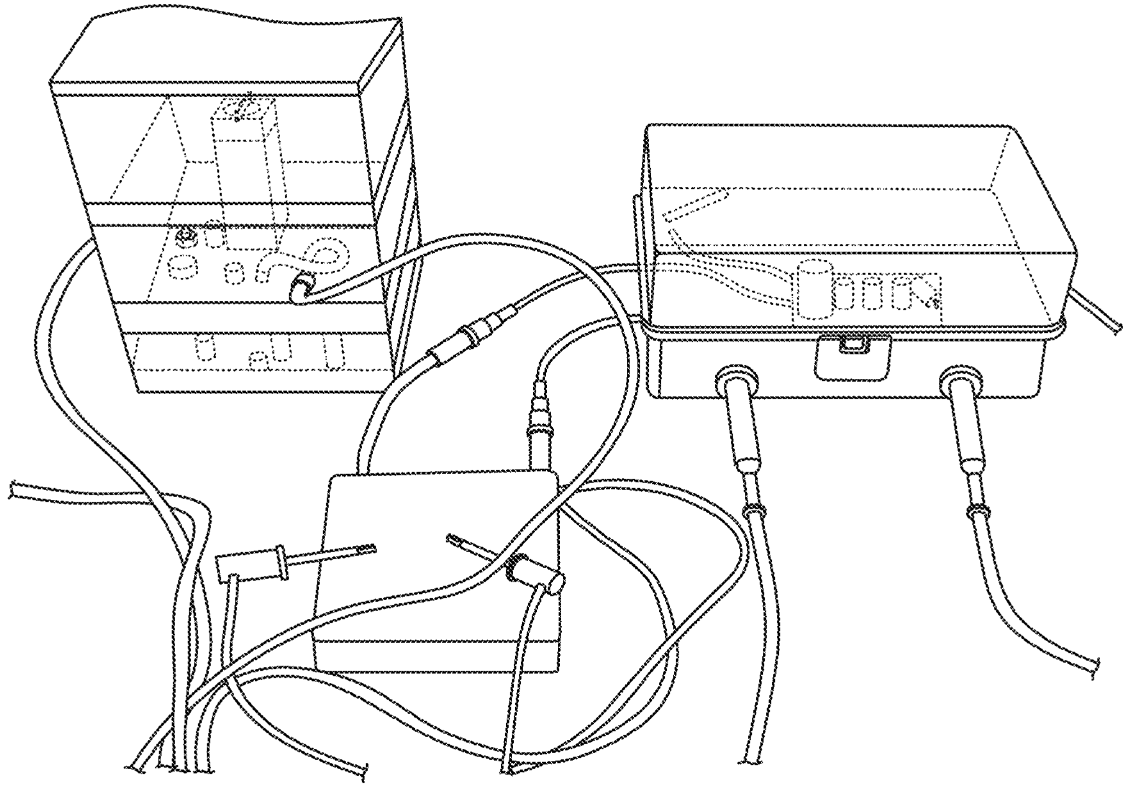
FIG. 19 is a photograph of the electroporation device 10 according to Example 3 after assembly.

As shown in FIG. 7 and FIG. 19, in Example 3, the device 10 was manufactured using a commercial cuvette having a 1 (mm) gap as the discharge generating portion 3, and the cells with the introduced foreign substance were produced using the manufactured device 10. The device 10 according to Example 3 is provided with the holding portion 2, the discharge generating portion 3, the conductive portion 4, the power amount control portion 5, and the power supply portion 6. The holding portion 2 that is the same as the holding portion 2 shown in FIG. 14 and FIG. 15 was used as the holding portion 2 (see bottom center of a photograph in FIG. 19). A product EC-001S manufactured by Nepa Gene Co., Ltd., and having a distance between a pair of electrodes of 1 (mm) was used as the discharge generating portion 3. The cuvette electrodes were housed in a cuvette electrode chamber (see upper left of the photograph in FIG. 19). The power amount control portion 5 is provided with the condenser 51 and the inductor 53. The inductor 53 was provided in parallel with the holding portion 2 and the condenser 51. In a similar manner to the device 1 according to Example 1, taking safety into account, the power supply portion 6 and the power amount control portion 5, which are the high-voltage generating components, were housed in a plastic case (see upper right of the photograph in FIG. 19). A DC power supply capable of generating 3 kV or more of voltage, formed by combining a cold cathode fluorescent lamp inverter (CCFL) and a Cockcroft-Walton circuit (CCW circuit), was used as the power supply portion 6.

Under each of Condition 6 to Condition 11 in which the electrostatic capacity of the condenser 51, the application time period, and the inductance of the inductor 53 are mutually different, using the same procedure as in Example 2, gene transfection experiments were performed in which the target cells were HEK293 cells, the foreign substance was the pCXLE-EGFP gene, and the aqueous solution was the culture medium OPTI-MEM buffer. In Condition 6, the electrostatic capacity of the condenser 51 is 7.3 (pF), the application time period is 30 (s), and the inductance of the inductor 53 is 1000 (μH). In Condition 7, the electrostatic capacity of the condenser 51 is 22 (pF), the application time period is 30 (s), and the inductance of the inductor 53 is 470 (μH). In Condition 8, the electrostatic capacity of the condenser 51 is 11 (pF), the application time period is 30 (s), and the inductance of the inductor 53 is 470 (μH). In Condition 9, the electrostatic capacity of the condenser 51 is 7.3 (pF), the application time period is 2 (min), and the inductance of the inductor 53 is 1000 (01). In Condition 10, the electrostatic capacity of the condenser 51 is 7.3 (pF), the application time period is 30 (s), and the inductance of the inductor 53 is 470 (μH). In Condition 11, the electrostatic capacity of the condenser 51 is 7.3 (pF), the application time period is 2 (min), and the inductance of the inductor 53 is 470 (μH).

Figure 20:
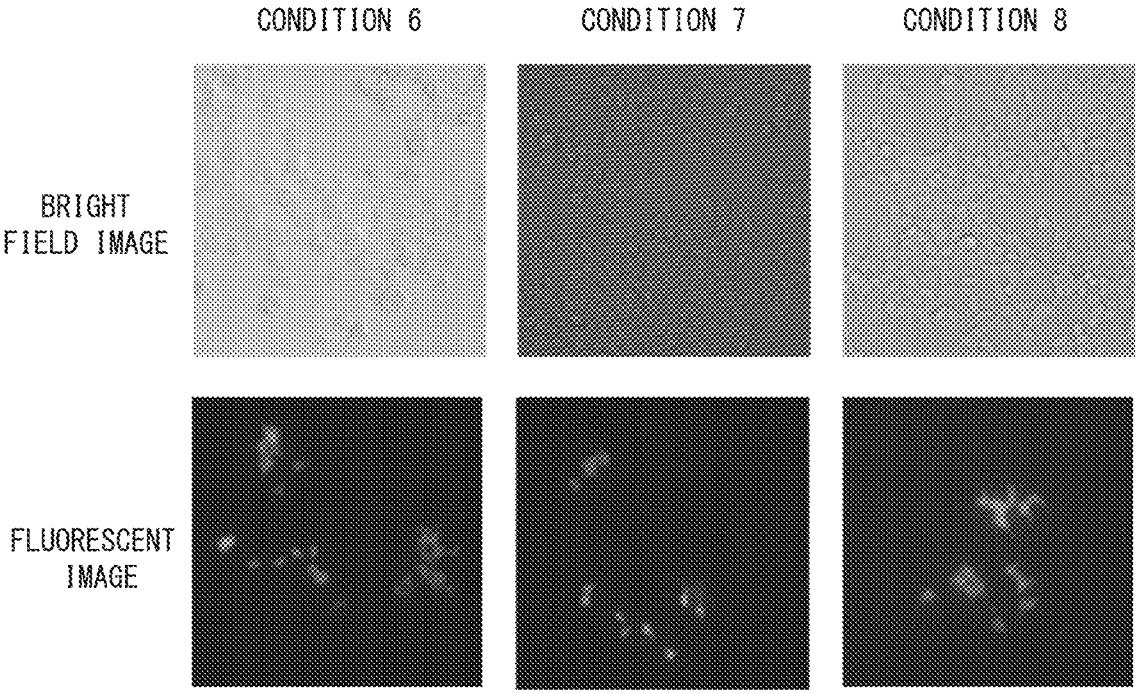
FIG. 20 includes observation images four days after an operation in which a fluorescent protein encoding gene has been introduced under each of Conditions 6 to 8, using the electroporation device 10 according to Example 3, and is a diagram showing microscope observation images in a bright field (20× observation magnification), and fluorescent images in a fluorescent field (20× observation magnification).
Figure 21:
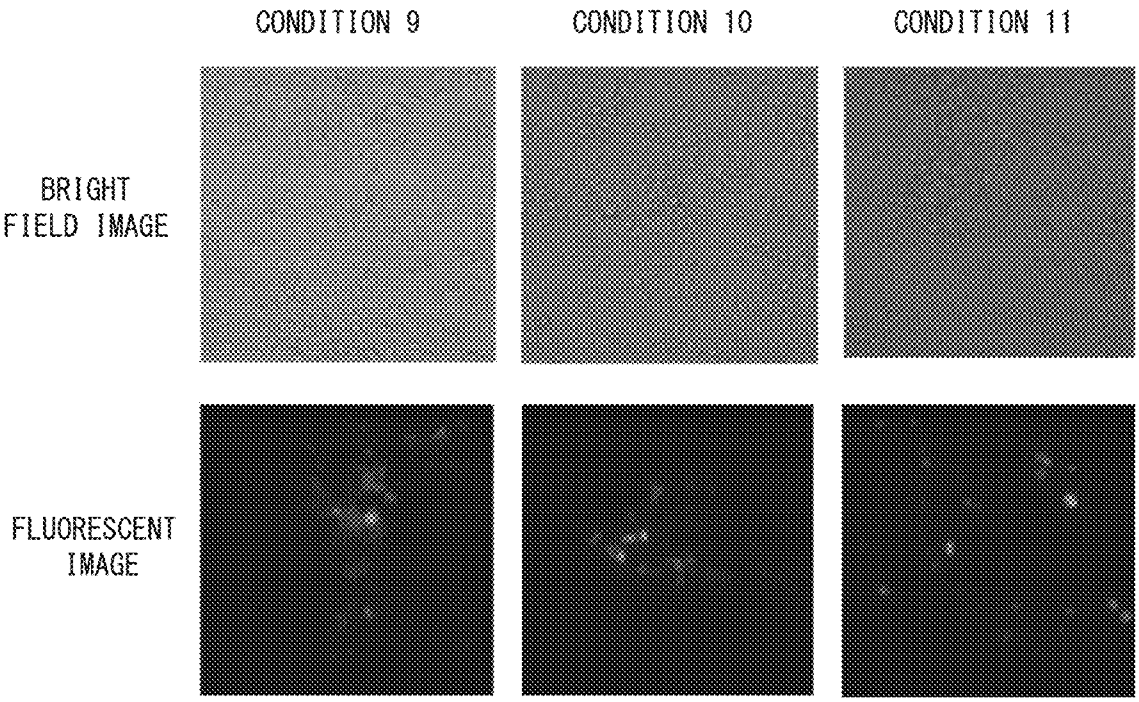
FIG. 21 includes observation images nine days after an operation in which a fluorescent protein encoding gene has been introduced under each of Conditions 9 to 11, using the electroporation device 10 according to Example 3, and is a diagram showing microscope observation images in a bright field (20× observation magnification), and fluorescent images in a fluorescent field (20× observation magnification).

For each of Condition 6 to Condition 11, when confirming the presence or absence of the expression of the fluorescent protein after 4 days or 9 days from the start of the gene transfection operation, in the negative control, the fluorescence signals due to the expression of the fluorescent protein were not detected from the target cells. As shown in FIG. 20 and FIG. 21, under each of Condition 6 to Condition 11, the fluorescence signals due to the expression of the fluorescent protein were detected from the target cells, and the expression of the fluorescent protein was confirmed. When the device 10 according to Example 3 was used, the gene transfection efficiency was 13 to 27% (n=12). From this, by using the device 10 according to Example 3, it was confirmed that the gene transfection into the nuclei of the target cells was possible.

7. Example 4

Figure 22:
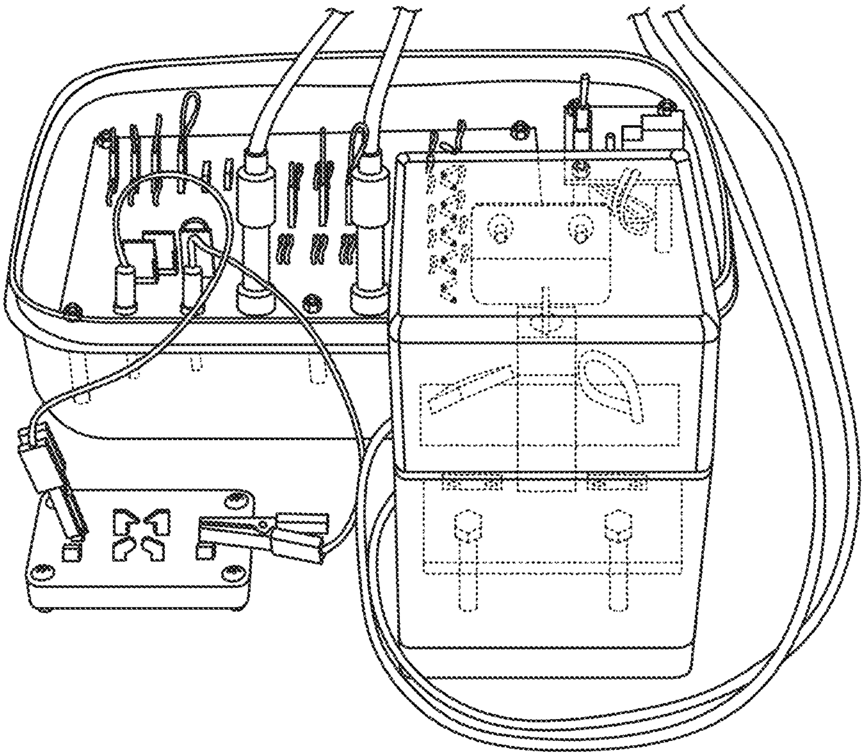
FIG. 22 is a photograph of the electroporation device 10 according to Example 4 after assembly.
Figure 23:
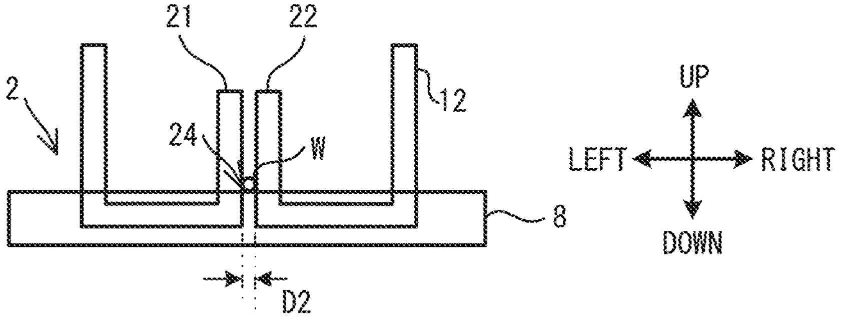
FIG. 23 is a schematic diagram of the holding portion 2 of the electroporation device 10 according to Example 4.

In Example 4 to Example 8, as shown in FIG. 8, FIG. 22, and FIG. 23, the device 10 was manufactured using a commercial cuvette having a 1 (mm) gap as the discharge generating portion 3, and the cells with the introduced foreign substance were produced using the manufactured device 10, using a similar procedure as that of Example 2 (note that the adjustment of the discharge cycle by the cycle adjustment portion 9 is not performed). The device 10 according to Example 4 is provided with the holding portion 2, the discharge generating portion 3, the conductive portion 4, the power amount control portion 5, and the power supply portion 6. As shown in FIG. 23, the holding portion 2 is provided with the pair of electrodes 21, 22 and with a placement portion 24. The pair of electrodes 21, 22 were processed and manufactured of an aluminum plate (A1000 series, pure aluminum based) having a thickness of 1.0 (mm). The pair of electrodes 21, 22 were held in the insulating resin plate (acrylic plate) 8 with the predetermined gap D2 therebetween (see lower left of a photograph in FIG. 22). The placement portion 24 is a section between the pair of electrodes 21, 22 within the upper surface of the insulating resin plate 8. The product EC-001S manufactured by Nepa Gene Co., Ltd., and having a distance between a pair of electrodes of 1 (mm) was used as the discharge generating portion 3. The cuvette electrodes were housed in a cuvette electrode chamber (see lower right of the photograph in FIG. 22). The power amount control portion 5 is provided with the condenser 51, the inductor 53, and the diode 54. The inductor 53 was provided in parallel with the holding portion 2 and the condenser 51. The diode 54 was provided in parallel with the holding portion 2, and the forward direction of the diode 54 was the direction from the condenser 51 to the inductor 53. A Schottky barrier diode suited to high speed switching and high frequency rectification (SCS205KGC, manufactured by Rohm Co. Ltd.) was used as the diode 54. In a similar manner to the device 1 according to Example 1, taking safety into account, the power supply portion 6 and the power amount control portion 5, which are the high-voltage generating components, were housed in a plastic case (see upper portion of the photograph in FIG. 22). A DC power supply capable of generating 3 kV or more of voltage, formed by combining the cold cathode fluorescent lamp inverter (CCFL) and the Cockcroft-Walton circuit (CCW circuit), was used as the power supply portion 6.

For each of Condition 12 and Condition 13, in which the electrostatic capacity of the condenser 51 was mutually different, and the electrostatic capacity of the condenser 60, the application time period, and the inductance of the inductor 53 were the same, using the same procedure as in Example 2, gene transfection experiments were performed in which the target cells were HEK293 cells, the foreign substance was the pCXLE-EGFP gene, and the aqueous solution was the culture medium OPTI-MEM buffer. The 4 (μL) droplet W of the cell suspension was placed on the placement portion 24 between the pair of electrodes 21, 22. In Condition 12 and Condition 13, the electrostatic capacity of the condenser 60 is 0 (pF), the application time is 30 (s), and the inductance of the inductor 53 is 5 (μH). In Condition 12, the electrostatic capacity of the condenser 51 is 3000 (pF), and in Condition 13, the electrostatic capacity of the condenser 51 is 1000 (pF). As a comparative example, the same experiments were conducted using NEPA21™ (Nepa Gene Co., Ltd.), which is a known gene transfection device.

Figure 24:
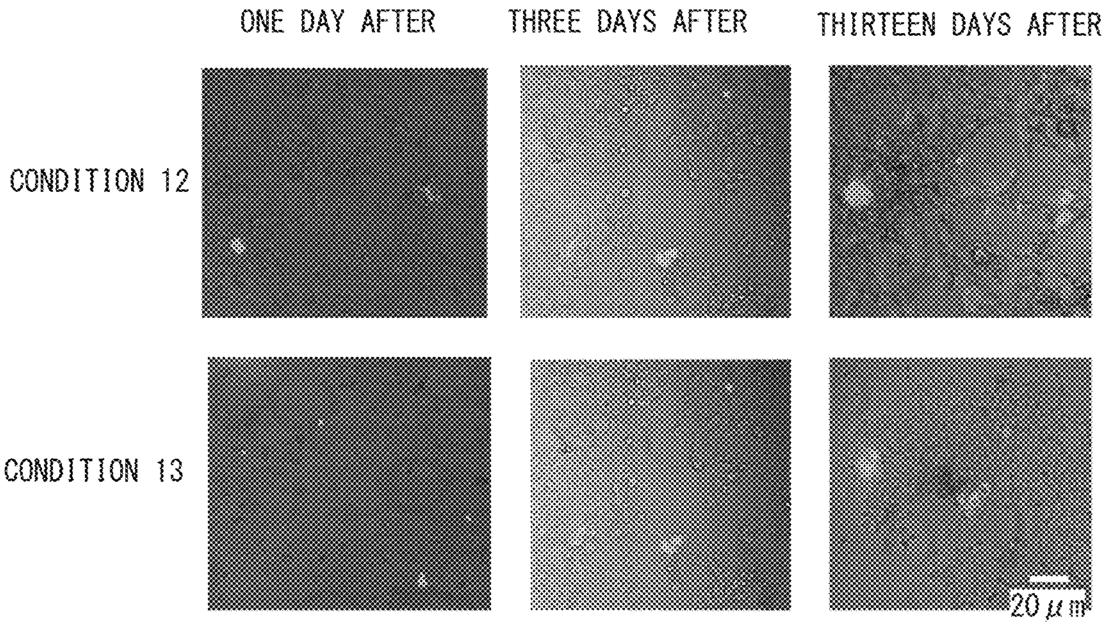
FIG. 24 includes observation images one day, three days, and thirteen days after an operation in which a fluorescent protein encoding gene has been introduced under each of Conditions 12 and 13, using the electroporation device 10 according to Example 4, and is a diagram showing microscope observation images in a bright field (20× observation magnification), and fluorescent images in a fluorescent field (20× observation magnification).

For each of Condition 12 and Condition 13, when confirming the presence or absence of the expression of the fluorescent protein after 1 day, 3 days, and 13 days, respectively, from the start of the gene transfection operation, in the negative control in which the voltage was not applied, the fluorescence signals due to the expression of the fluorescent protein were not detected from the target cells. As shown in FIG. 24, under each of Condition 12 and Condition 13, after the gene transfection operation, the fluorescence signals due to the expression of the fluorescent protein were detected from the target cells, and the expression of the fluorescent protein was confirmed. In Condition 12 and Condition 13, the expression of the introduced gene was observed after 1 day from the gene transfection operation. In the case of using a device of the comparative example, and in the case of using the device 10 according to Example 4, the fluorescence signals were observed, using the fluorescence microscope, after 2 days from the gene introduction operation, and there was almost no difference in gene transfection efficiency between the case of the device of the comparative example and the case of the device 10 according to Example 4. In the case of the device 10 according to Example 4, it was conceived that, even after the second day from the gene transfection operation, a color of a pH indicator of the liquid culture medium changed to a color considered to be caused by the cells proliferating and causing a bias toward acidity, and the cells were also proliferating after the gene transfection operation. In contrast to this, in the case of the device of the comparative example, a change in the color of the liquid culture medium after the second day from the gene transfection operation was slight, and it was conceived that the cells were not proliferating after the gene transfection operation. From this, in comparison to the case of the device of the comparative example, in the case of the device 10 according to Example 4, it is conceived that cell toxicity is extremely low, and a state of the cells is good, and it was suggested, for example, that the device 10 according to Example 4 can be favorably applied to gene transfection requiring a low cell toxicity by the gene transfection operation, such as gene transfection to plant cells and the like.

8. Example 5

In Example 5, the same device 10 as that of Example 4 was used, and the cells with introduced foreign substance were produced. Using the same procedure as in Example 2, a gene transfection experiment was performed in which the target cells were floating human HL60 cell lines, the foreign substance was the pCXLE-EGFP gene, and the aqueous solution was the culture medium OPTI-MEM buffer. The 4 (μL) droplet W of the cell suspension was placed on the placement portion 24 between the pair of electrodes 21, 22. The electrostatic capacity of the condenser 60 was 0 (pF), the electrostatic capacity of the condenser 51 was 2000 (pF), the application time period was 30 (s), and the inductance of the inductor 53 was 5 (μH). As a comparative example, the same experiment was conducted using NEPA21™ (Nepa Gene Co., Ltd.), which is the known gene transfection device.

Figure 25:
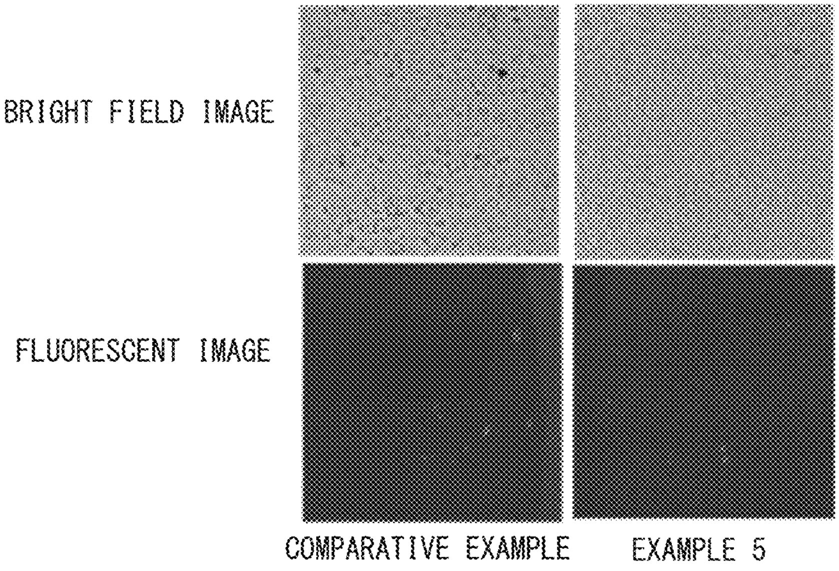
FIG. 25 includes observation images two days after an operation in which a fluorescent protein encoding gene has been introduced, respectively using a comparative example and the electroporation device 10 according to Example 5, and is a diagram showing microscope observation images in a bright field (20× observation magnification), and fluorescent images in a fluorescent field (20× observation magnification).
Figure 26:
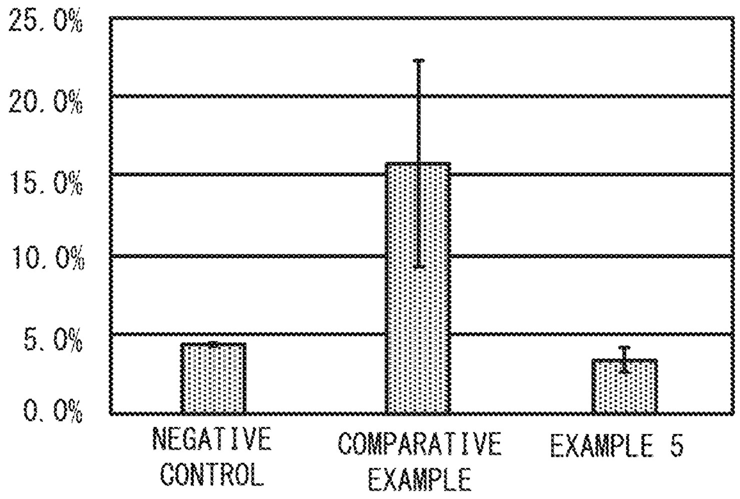
FIG. 26 is a graph showing results of comparing death rates of cells, which is a number of dead cells in relation to all the cells, on the basis of microscope observation images in a bright field two days after an operation in which a fluorescent protein encoding gene has been introduced, respectively using the comparative example, the electroporation device 10 according to Example 5, and a negative control.

As shown in FIG. 25, when the device of the comparative example was used and when the device 10 according to Example 5 was used, when observing the fluorescence signals using the fluorescence microscope after 2 days from the gene transfection operation, the fluorescence signals due to the expression of the fluorescent protein were detected from the target cells in each of the comparative example and Example 5, and the expression of the fluorescent protein was confirmed. In the negative control in which the voltage was not applied, the fluorescence signals due to the expression of the fluorescent protein were not detected from the target cells. When the device of the comparative example and the device 10 according to Example 5 were used, when observing the fluorescence signals using the fluorescence microscope after 2 days from the gene transfection operation, there was almost no change in the gene transfection efficiency between the device of the comparative example and the device 10 according to Example 5. However, as a result of dyeing dead cells using trypan blue, and comparing, using a bright field image, a death rate that is a number of the dead cells with respect to all the cells, a significant difference was observed between the two examples. Specifically, as shown in FIG. 26, in the case of the device of the comparative example, the death rate of the cells was 15.8% (±6.5), while in the case of the device 10 according to Example 5, the death rate of the cells was 3.4% (±0.8). In comparison to the device of the comparative example, in the case of the device 10 according to Example 5, the cell toxicity was low, and it was conceived that a state of the cells was good. The death rate of the cells in the case of the device 10 according to Example 5 was similar to the death rate of the cells in the negative control in which the voltage was not applied to the cell suspension, which was 4.4% (±0.1) (n=3).

9. Example 6

In Example 6, iPS cells were produced using the same device 10 as in Example 4. The target cells were lymph T cells in the blood, the foreign substances were Yamanaka factors (OCT-3/4, SOX2, KLF4, L-MYC) and the EOS-EGFP vector that is a marker expressing the green fluorescent protein (EGFP) when the Yamanaka factors are introduced into the cells and undifferentiated, and the aqueous solution was the culture medium OPTI-MEM buffer. The target cells were adjusted such that approximately 80,000 target cells were inside the 4 (μL) droplet W of the cell suspension, and a gene transfection experiment was performed using the same procedure as Example 2. The 4 (μL) droplet W of the cell suspension was placed on the placement portion 24 between the pair of electrodes 21, 22. In Condition 14, the electrostatic capacity of the condenser 60 was 4000 (pF), the electrostatic capacity of the condenser 51 was 1000 (pF), the application time period was 15 (s), and the inductance of the inductor 53 was 5 (01). In condition 15, the electrostatic capacity of the condenser 60 was 1500 (pF), the electrostatic capacity of the condenser 51 was 500 (pF), the application time period was 15 (s), and the inductance of the inductor 53 was 10 (01). A condition under which the voltage was not applied to the cell suspension was the negative control.

Figure 27:
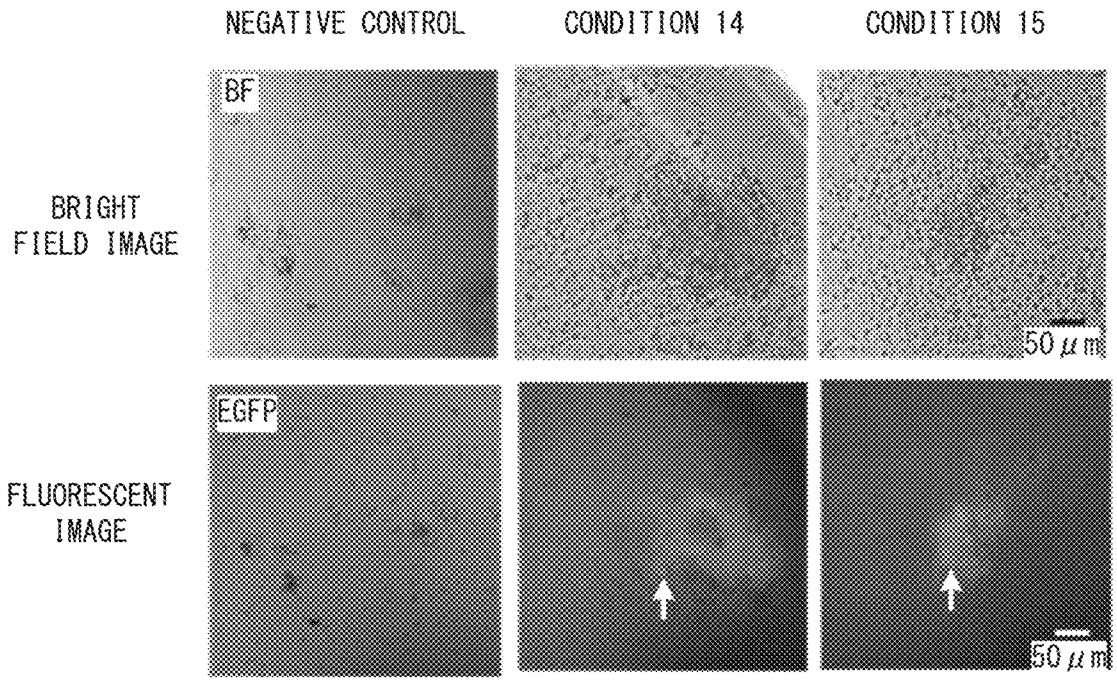
FIG. 27 includes observation images sixteen days after an operation in which, using the electroporation device 10 according to Example 6, and under a negative control, and Conditions 14 and 15, respectively, Yamanaka factors and the EOS-EGFP vector expressing the enhanced green fluorescent protein (EGFP) when the Yamanaka factors are introduced into the cells and undifferentiated are introduced, and is a diagram showing microscope observation images in a bright field (20× observation magnification), and fluorescent images in a fluorescent field (20× observation magnification).

As shown in FIG. 27, for each of the conditions, when observing the fluorescence signals using a fluorescence microscope after 16 days from the gene transfection operation, in each Condition 14 and Condition 15 of Example 6, the fluorescence signals due to the expression of the fluorescent protein were detected from the target cells, and the expression of the fluorescent protein after the gene transfection was confirmed. In the negative control in which the voltage was not applied, the fluorescence signals due to the expression of the fluorescent protein was not detected from the target cells. From the results of Example 6, it was confirmed that the device 10 according to Example 6 can be favorably used for producing iPS cells also.

10. Example 7

In Example 7, it was confirmed whether or not genome editing and transfection of multiple gene types are possible using the same device 10 as in Example 4. Using the same procedure as in Example 2, gene transfection experiments were performed in which the target cells were HEK293 cells, the foreign substances were Cas9-RFP Lenti Plasmid (manufactured by Sigma-Aldrich Inc.) capable of expressing the CAS9 enzyme for performing gene editing and red fluorescent protein (RFP), and pX330-Cetn1/1 and pCAG-EGxxFP-Cetn1 (manufactured by Addgene, developed by the Igawawa Laboratory, Osaka University) which are two types of plasmid DNA capable of expressing GFP when the genome thereof is edited, and the aqueous solution was the culture medium OPTI-MEM buffer. The 4 (μL) droplet W of the cell suspension was placed on the placement portion 24 between the pair of electrodes 21, 22. In Condition 16, the electrostatic capacity of the condenser 60 was 0 (pF), the electrostatic capacity of the condenser 51 was 3000 (pF), the application time period was 60 (s), and the inductance of the inductor 53 was 5 (μH). In Condition 17, the electrostatic capacity of the condenser 60 was 0 (pF), the electrostatic capacity of the condenser 51 was 2000 (pF), the application time period was 60 (s), and the inductance of the inductor 53 was 5 (μH). In Condition 18, the electrostatic capacity of the condenser 60 was 4000 (pF), the electrostatic capacity of the condenser 51 was 1000 (pF), the application time period was 60 (s), and the inductance of the inductor 53 was 5 (μH). A condition under which the voltage was not applied to the cell suspension was the negative control.

Figure 28:
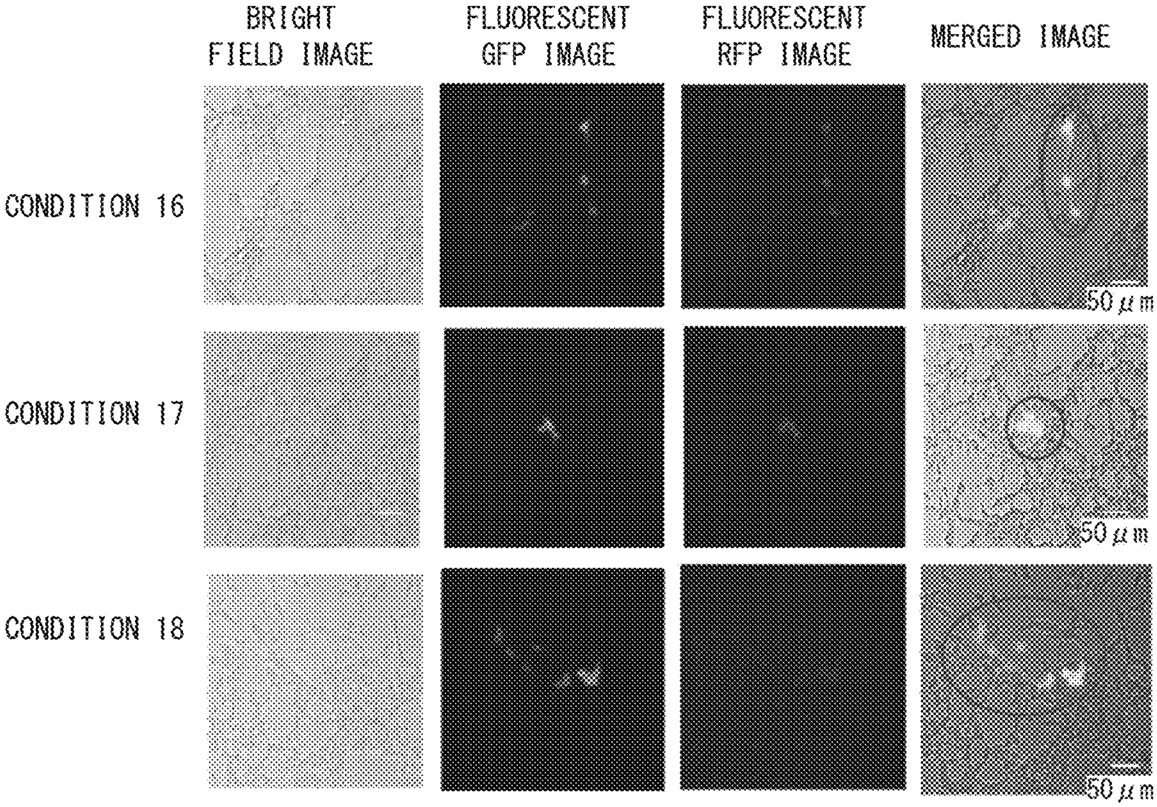
FIG. 28 includes observation images two days after an operation in which a fluorescent protein encoding gene has been introduced, using the electroporation device 10 according to Example 7, and under Conditions 16 to 18, respectively, and includes superimposed images in which microscope observation images in a bright field (20× observation magnification) and fluorescent images in GFP and RFP (Red fluorescent protein) fluorescent fields (20× observation magnification) are superimposed.

For Condition 16 to Condition 18, the fluorescence signals were observed using the fluorescence microscope after 2 days from the gene transfection operation. With respect to the GFP fluorescence signals, a mercury lamp was used as a light source, excitation light in the vicinity of the 490 nm wavelength was irradiated via a filter, and green fluorescence signals were observed, via a filter, in the vicinity of the 510 nm wavelength. With respect to the RFP fluorescence signals, the mercury lamp was used as the light source, excitation light in the vicinity of the 590 nm wavelength was irradiated via a filter, and red fluorescence signals were observed, via a filter, in the vicinity of the 610 nm wavelength. In each of Condition 16 to Condition 18, the target cells indicating the GFP fluorescence signals were confirmed. In the negative control in which the voltage was not applied, the fluorescence signals due to the expression of the GFP were not detected from the target cells. In this way, it was confirmed that genome editing of HEK293 cells is possible using the device 10 according to Example 7. Furthermore, in one of the target cells, the cell was confirmed that indicated each of the GFP fluorescence signals and the RFP fluorescence signals. A row of images furthest to the right side in FIG. 28 are superimposed images in each of which a bright field image, a fluorescent GFP image, and a fluorescent RFP image are superimposed, and in the superimposed images in FIG. 28, the target cells indicating yellow signals represented by a whitish color show that the three types of plasmid DNA have been transduced. As shown in FIG. 28, in each of Condition 16 to Condition 18, the cells indicating the yellow signals were confirmed from the superimposed images. From this, it was confirmed that, by performing the gene transfection operation once, it is possible to introduce a plurality of foreign substances at one time into the HEK293 cells (in other words, the transfection of multiple gene types is possible), using the device 10 according to Example 7.

11. Example 8

In Example 8, cells with an introduced foreign substance were produced, and a gene transfection success rate in mammal HEK cells was confirmed, using the same device 10 as in Example 4. Using the same procedure as in Example 2, gene transfection experiments were performed in which the target cells were mammal HEK cells, the foreign substance was the pCMV-EGFP gene, and the aqueous solution was the culture medium OPTI-MEM buffer. The 4 (μL) droplet W of the cell suspension was placed on the placement portion 24 between the pair of electrodes 21, 22. In Condition 19, the electrostatic capacity of the condenser 60 was 4000 (pF), the electrostatic capacity of the condenser 51 was 1000 (pF), the application time period was 15 (s), and the inductance of the inductor 53 was 5 (μH). In Condition 20, the electrostatic capacity of the condenser 60 was 4000 (pF), the electrostatic capacity of the condenser 51 was 1000 (pF), the application time period was 30 (s), and the inductance of the inductor 53 was 5 (01). In Condition 21, the electrostatic capacity of the condenser 60 was 0 (pF), the electrostatic capacity of the condenser 51 was 3000 (pF), the application time period was 15 (s), and the inductance of the inductor 53 was 5 (μH). In Condition 22, the electrostatic capacity of the condenser 60 was 0 (pF), the electrostatic capacity of the condenser 51 was 3000 (pF), the application time period was 30 (s), and the inductance of the inductor 53 was 5 (μH).

Figure 29:
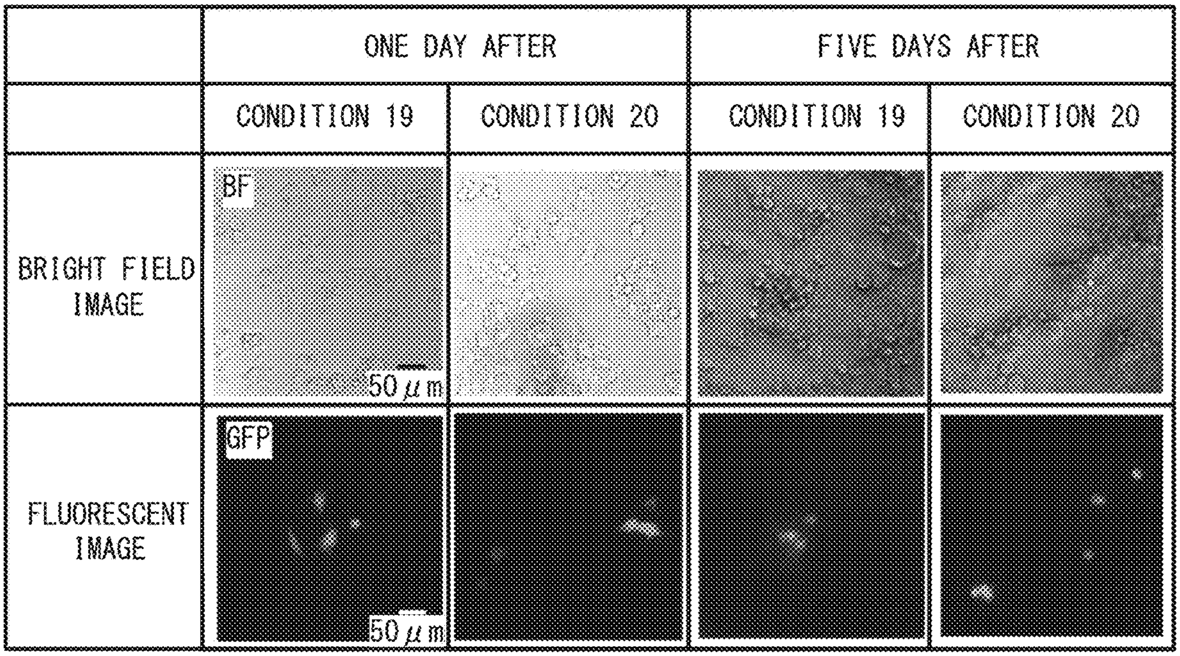
FIG. 29 includes microscope observation images in a bright field (20× observation magnification) and fluorescent images in a GFP fluorescent field (20× observation magnification) one day and five days after an operation in which a fluorescent protein encoding gene has been introduced, using the electroporation device 10 according to Example 8, and under Conditions 19 and 20, respectively.

For each of Condition 19 to Condition 22, when observing the fluorescence signals using a fluorescence microscope after 2 days from the gene transfection operation, the expression of the fluorescent protein after gene transfection was confirmed under each of the conditions of Example 8, and the gene transfection efficiency was 0.02 to 0.13%. The gene transfection success rate was 100% in each of the conditions. The gene transfection success rate is a number of successful samples for the gene transfection in relation to a total of observed samples, where one cell suspension is one sample, and the success rate is obtained by adding up successes and failures of the gene transfection for each of the samples. In a device of known art that performs the electroporation inside the droplet in oil, due to shorting and the like of the device during the gene transfection, the gene transfection success rate when recovering one droplet was approximately 50%. Further, when the device of known art that performs the electroporation inside the droplet in oil was used, almost no expression of the transduced gene was observed up to 2 days after the gene transfection operation, and the expression of the transduced gene was confirmed from 3 days from the gene transfection operation. In contrast to this, in the device 10, the gene transfection success rate in Example 8 is 100%. Furthermore, as shown in FIG. 29, when the device 10 according to Example 8 was used, the fluorescence signals due to the expression of the fluorescent protein were observed from the target cells after 1 day from the gene transfection operation, and the expression of the transduced gene was confirmed. From this, it can be said that when the device 10 is used, the gene transfection success rate is stable, in comparison to the device of known art that performs the electroporation inside the droplet in oil.

With the device 1, 10 and the method for producing the cells with the introduced foreign substance according to the above-described embodiment, the following effects can be obtained. The device 1, 10 can apply the pulsed high-voltage electric current of the short time period, without causing the solution containing the foreign substance and the cells to reciprocate in the oil. Thus, since there is no need to recover the sample from the oil, the device 1, 10 can simplify the operation to recover the sample after the reaction, in comparison to the device performing the electroporation in the droplet in the oil. The device 1, 10 does not require the expensive pulse generator that can output the rectangular pulsed electric current in accordance with the program, which is indispensable in the general electroporation device. Since the configuration of the device 1, 10 is simple, the device 1, 10 is manufactured at low cost. The discharge generating portion 3 includes the pair of electrodes 31, 32 disposed with the predetermined gap therebetween, and the arc discharge is generated between the pair of electrodes 31, 32. Thus, with the relatively simple configuration, the device 1, 10 can supply the pulsed high-voltage electric current to the holding portion 2 for the short ON period in comparison to the known art.

In the device 1, 10, the reactions of the electroporation and the gene transfection are performed in the solution that is still, and are implemented in a stable manner without being influenced by a state of reciprocating movement in the solution. Since the device 1, 10 uses the electric action applied to the solution held by the holding portion 2, the special reagent is not required, and the device 1, 10 can suppress running costs in comparison to a case in which the foreign substance is introduced into the target cell using a chemical method. Furthermore, with the device 1, 10, there is no fear of oncogenesis or the like of the target cells caused by toxicity and antigenicity to the target cells, as occurs in a biological approach using a virus. By generating the pulsed electric current using the arc discharge, the device 1, 10 can shorten the time period of the ON period (to approximately several microseconds) of the pulsed electric current applied to the target cells, in comparison to the known device. Thus, while making the electric force instantaneously applied to the target cells larger in comparison to the known device, the device 1, 10 can cause an overall amount of electric energy applied to the target cells to be smaller in comparison to the known device, and thus, can suppress the damage imparted to the target cells in comparison to the known device. It is thus conceivable that the transduced cells can be obtained with the favorable probability of survival. Since the device 1, 10 does not use the oil, the device 1, 10 can also be applied to the target cells for which not using the oil is preferable. The target cells for which not using the oil is preferable include particular plant cells, for example.

The power amount control portion 5 of the device 1 shown in FIG. 3 is provided with the condenser 51 that is electrically connected to the power supply portion 6 and the discharge generating portion 3, accumulates the electric charge as a result of the voltage applied by the power supply portion 6, and discharges the accumulated electric charge to the discharge generating portion 3. The device 1 shown in FIG. 3 can prescribe the amount of electric energy of the pulsed electric current supplied to the holding portion 2, using the electrostatic capacity of the condenser 51. The discharge generating portion 3 of the device 10 shown in FIG. 5 to FIG. 8 is electrically connected to the power supply portion 6. The power amount control portion 5 is provided with the condenser 51 that is electrically connected to the holding portion 2, and that accumulates the electric charge of the pulsed electric current supplied to the holding portion 2. The device 10 shown in FIG. 5 to FIG. 8 can prescribe the amount of electric energy of the pulsed electric current supplied to the holding portion 2, using the electrostatic capacity of the condenser 51. The device 1, 10 is provided with the power supply portion 6 capable of supplying the high-voltage DC power of 3 kV or more. With the device 1, 10, there is no need to separately prepare the power supply portion 6.

The leading ends of the pair of electrodes 31, 32 of the discharge generating portion 3 of the device 1 according to Example 2 are formed in the hemispherical shape. In comparison to a case in which the device 1 according to Example 2 includes electrodes having a different shape, the device 1 can cause the discharge generating portion 3 to generate the arc discharge of an even higher discharge voltage.

The power amount control portion 5 of the device 1 according to Example 1 is provided with the dark current control portion 52 in order to suppress the influence of the dark current generated in the discharge generating portion 3. Even when the dark current is generated between the pair of electrodes 31, 32 of the discharge generating portion 3, the device 1 according to Example 1 can cause the discharge generating portion 3 to generate the arc discharge in a stable manner.

The device 1 according to Example 2 includes the cycle adjustment portion 9, and applies the voltage to the discharge generating portion 3 in the cyclical manner at the predetermined interval. The device 1 can easily change the conditions of a length of the interval and a number of repetitions. Thus, in the device 1 according to Example 2, reaction conditions suited to the sample can be easily set. The power amount control portion 5 of the device 10 according to Example 3 is provided with the inductor 53 that is connected in parallel to the holding portion 2 and the condenser 51, and that applies the counter electromotive force to the discharge generating portion 3. Using the action of the inductor 53, the device 10 can apply the voltage to the target cell in both the forward and reverse directions, via the holding portion 2.

The power amount control portion 5 of the device 10 according to Example 4 is provided with the diode 54 that is connected in parallel with the holding portion 2 and for which the forward direction is the direction in which the electric current discharged from the condenser 51 flows. In the device 10 according to Example 4, the waveform of the pulsed electric current that is applied to the holding portion 2 can be caused to be a waveform in which, due to the rectification by the diode 54, a negative component in the attenuated vibration waveform pulse is eliminated. In the device 10 according to Example 3 that is not provided with the diode 54, the expression of the introduced gene was confirmed after 10 days from the gene transfection operation, while in contrast, in the device 10 according to Example 4 that is provided with the diode 54, the expression of the introduced gene was confirmed after 1 day from the gene transfection operation. From this, it is conceivable that, in comparison to the device 10 that is not provided with the diode 54, the device 10 according to Example 4 that is provided with the diode 54 can reduce the damage to the target cells caused by the gene transfection operation.

The known device that performs the electroporation in the solution in the oil performs the electroporation on the target cells in the solution by applying the electric charge to the droplet that comes into contact with the electrode when the solution reciprocates between the electrodes (refer to Japanese Laid-Open Patent Publication No. 6269968, for example). Thus, in this device, a shutdown of the circuit by the insulting oil is performed, and in comparison to the known device, the gene transfection with respect to an extremely low quantity of sample is possible with low cytotoxicity. However, in the above-described known device, the reciprocating movement of the droplet tends to become unstable, and there is a problem that the gene transfection is not stable. In contrast to this, the device 1, 10 can apply the electric charge to the solution under conditions similar to when performing the transfection in the droplet in the oil, in a state in which the solution (the cell suspension) that is the reaction field is still. In other words, the device 1, 10 succeeds in reproducing reaction conditions of the device using the known droplet in the oil, without causing the reciprocating movement of the droplet in the oil. The device 1, 10 can apply the electric charge to the solution in an insulating oil-free state, and thus can eliminate the influence of the oil on the target cells. Furthermore, in the device 1, 10, it is possible to freely set various conditions of the arc discharge (the amount of electric energy of the pulsed electric current supplied to the holding portion 2, the magnitude of the voltage, the cycle at which the voltage is applied to the discharge generating portion 3, and the like), and thus, optimal conditions for the sample can be systematically explored. Thus, in comparison to the known device, the general-purpose versatility of the device 1, 10 is high. Moreover, the device 1, 10 can be kept to an overall size of approximately 10 (cm)×10 (cm)×10 (cm), and the device 1, 10 is thus portable.

The electroporation device and the method of producing the cells with the introduced foreign substance according to the present invention are not limited to the above-described embodiments, and various modifications may be made insofar as they do not depart from the scope of the present invention. As long as the electroporation device is provided with the holding portion, the discharge generating portion, the conductive portion, and the power amount control portion, a remaining configuration may be changed or omitted as appropriate. A mode of the electrical circuits, and the shape and the like of the discharge generating portion are different in each of the technologies illustrated by Examples 1 to 8, but some or all of the devices can be used in combination as appropriate. In order to suppress cytotoxicity rising as a result of raising the amount of electric energy supplied to the target cell, at least one of an electrical resistance, a voltage dividing condenser, or a condenser that regulates electrostatic capacity may be provided between the discharge generating portion and the holding portion. The size of the electroporation device may be changed as appropriate depending on a volume and the like of the solution that is the target of the processing. A number of the holding portion, the discharge generating portion, the conductive portion, and the power amount control portion of the electroporation device may be changed as appropriate. For example, in the electroporation device, a plurality of the holding portions may be connected in series or in parallel with respect to the single discharge generating portion.

Figure 17:
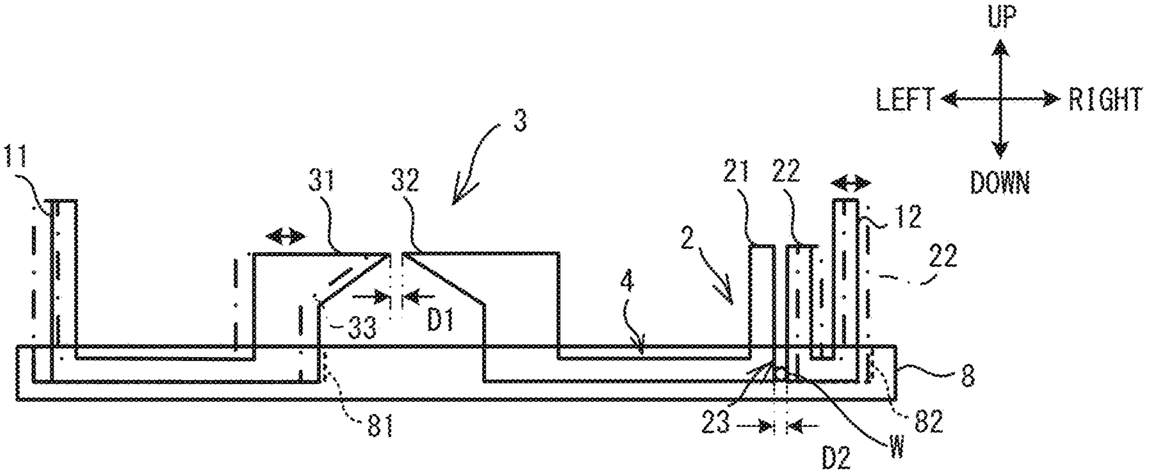
FIG. 17 is schematic diagram of the holding portion 2, the discharge generating portion 3, and the conductive portion 4 of the electroporation device 1 according to a modified example.

The discharge generating portion 3 may be formed such that the predetermined gap between the pair of electrodes is changeable. In the device 1, for example, at least one of the pair of electrodes may be slidable with respect to the other. Specifically, the configuration of the device 1 shown in FIG. 9 may be modified as in the modified example shown in FIG. 17. In the discharge generating portion 3 of the modified example shown in FIG. 17, a length in the left-right direction of a slit 81 for disposing the electrode 31 is formed in accordance with a slidable range of the electrode 31, and thus, of the pair of electrodes 31, 32, the one electrode 31 can slide with respect to the other electrode 32. In a similar manner, the holding portion 2 may be formed such that the gap between the pair of electrodes 21, 22 is changeable. For example, the configuration of the device 10 shown in FIG. 9 may be changed as shown in FIG. 17. In the holding portion 2 of the modified example shown in FIG. 17, a length in the left-right direction of a slit 82 for disposing the electrode 22 is formed in accordance with a slidable range of the electrode 22, and thus, of the pair of electrodes 21, 22, the one electrode 22 can slide with respect to the other electrode 21. In the electroporation device, a configuration may be adopted in which both the electrodes of at least one of the pair of electrodes provided in holding portion or the discharge generating portion can slide in a direction to change the distance between the electrodes.

Figure 18:
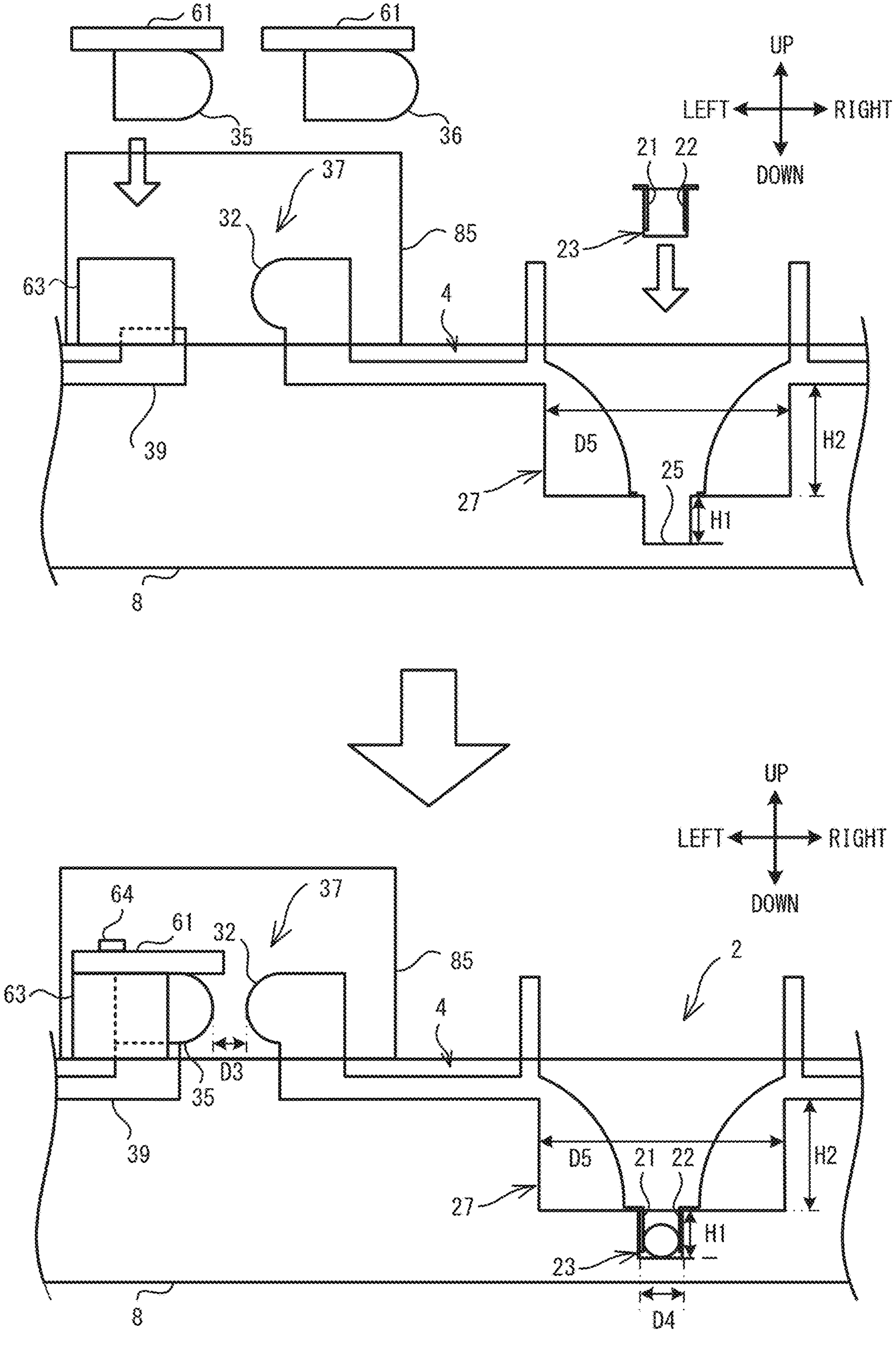
FIG. 18 is schematic diagram of the holding portion 2, a discharge generating portion 37, and the conductive portion 4 of the electroporation device 1 according to a modified example.

In another example, a plurality of electrode pairs may be prepared in which distances between the pairs of electrodes provided in the discharge generating portion are different, and the predetermined gap between the pair of electrodes may be changeable by detachably fixing one of the plurality of electrode pairs using a screw or the like. For example, the configuration of the device 1 shown in FIG. 14 may be changed as shown in FIG. 18. A discharge generating portion 37 according to a modified example is provided with a wiring line 39, a mounting portion 63, an electrode 32, a plurality of electrodes 35 and 36, and attachment plates 61. One of the plurality of electrodes 35 and 36 that is selected as one of the electrodes for the pair of the electrodes that generates the arc discharge is detachably fixed to the mounting portion 63. The mounting portion 63 is provided in the vicinity of the wiring line 39. Each of the plurality of electrodes 35 and 36 is fixed to the attachment plate 61. The number of the plurality of electrodes may be changed as appropriate. The attachment plate 61 is fixed to the mounting portion 63 by a screw 64. In the state in which the attachment plate 61 is fixed to the mounting portion 63, each of the plurality of electrodes 35 and 36 is electrically connected to the wiring line 39. In the state in which the attachment plate 61 is fixed to the mounting portion 63, the distance D1 between each of the plurality of electrodes 35 and 36 and the electrode 32 is different. The operator selects, from the plurality of electrodes 35 and 36, the electrode for which the predetermined distance between the plurality of electrodes provided in the discharge generating portion 37 is a desired length, and fixes the selected electrode to the mounting portion 63. When the attachment plate 61 is fixed to the mounting portion 63, the position of the one electrode with respect to the electrode 32 can be easily determined such that the distance between the electrodes is the desired distance. The electroporation device may be configured such that both of the pair of electrodes provided in the discharge generating portion can be attached to and removed from the wiring line that is electrically connected to the pair of electrodes. In the modified examples shown in FIG. 17 and FIG. 18, a leading end shape, a size, and an arrangement of the electrodes of the discharge generating portion, and a shape, size, and arrangement of the electrodes of the holding portion may be changed as appropriate.

The conditions for causing the pair of electrodes of the discharge generating portion to generate the arc discharge are subject to the influence of components of gases present in the surroundings, humidity, and the like. For this reason, in order to reduce the influence of the surrounding atmosphere, and cause the arc discharge to be generated in a stable manner, the discharge generating portion may be disposed in a closed container, and may be disposed in dry air, in a rare gas atmosphere such as argon or the like. In this case, for example, the electroporation device as shown in FIG. 18 may be provided with a container 85 that can seal a space surrounding the discharge generating portion 37, and the interior of the container 85 may be filled with the dry air, rare gas, or the like. In order to separate the discharge generating portion from the outside environment as much as possible, the discharge generating portion may be a commercially available electroporation cuvette provided with a pair of electrodes, a light bulb in which the filaments are cut, or the like.

The electroporation device may be configured such that at least one selected from the group of the holding portion, the discharge generating portion, the conductive portion, and the power amount control portion can be detachably provided. In the electroporation device, for example, the configuration of the device 1 shown in FIG. 14 may be changed as shown in FIG. 18, and the container 23 and the pair of electrodes 21, 22 of the holding portion 2 may be detachably provided. In the modified example shown in FIG. 18, the holding portion 2 of the electroporation device includes the detachable container 23 and pair of electrodes 21, 22. The container 23 is formed in a bottomed cylindrical shape, of an insulating material. The pair of electrodes 21, 22 extend in the up-down direction along side surfaces of the container 23. As shown in lower portion of FIG. 18, the container 23 is detachably housed in a recessed portion 25. When the container 23 is housed in the recessed portion 25, each of the pair of electrodes 21, 22 is electrically connected to the conductive portion 4. When the electroporation device is provided with the detachable holding portion, taking into account contamination of another sample or the like, for example, the holding portion can be disposed of after use. With the electroporation device, the holding portion can be replaced in accordance with deterioration or the like of the holding portion. When the discharge generating portion 3 is replaceable, even when deterioration occurs, such as an oxide film on the surface of the pair of electrodes of the discharge generating portion, by replacing with a new component, the arc discharge can be generated between the pair of electrodes under the same conditions, in which an influence of the deterioration of the discharge generating portion is eliminated. The electroporation device may omit the power supply portion. In this case, a power supply portion may be provided separately from the electroporation device, and may be connected to the electroporation device.

Figure 30:
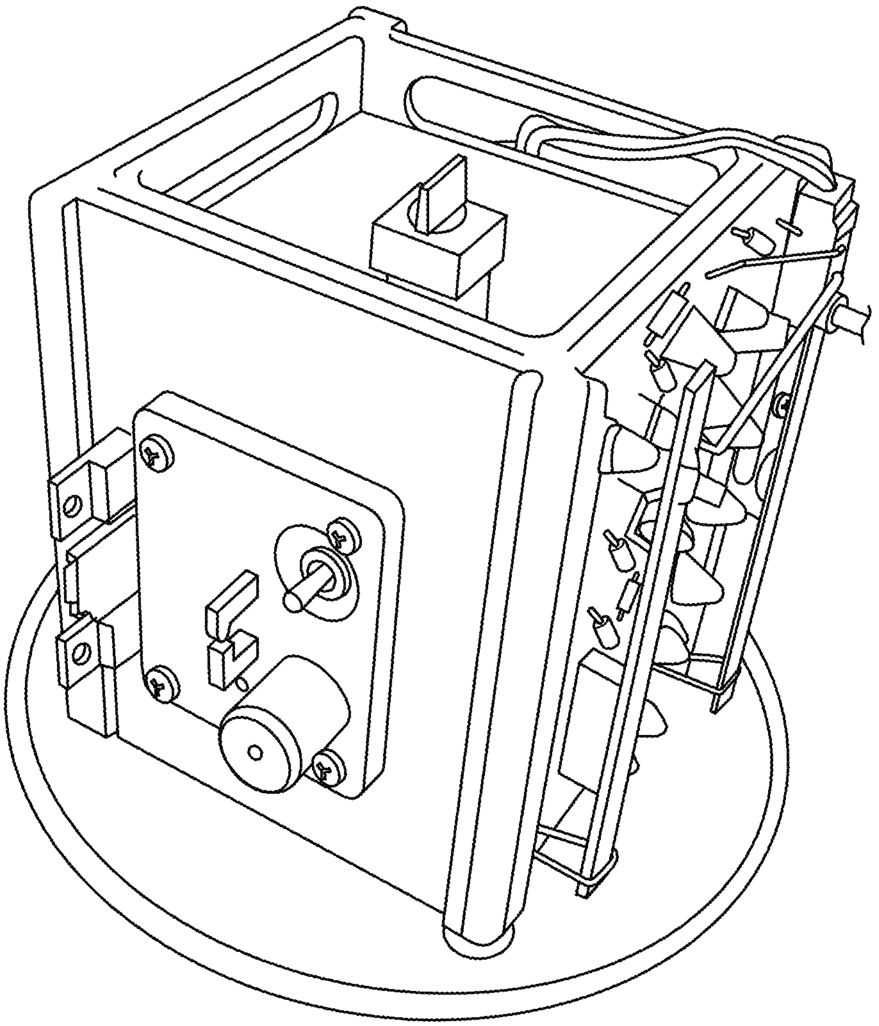
FIG. 30 is a photograph of the electroporation device 10 according to a modified example after assembly.
Figure 31:
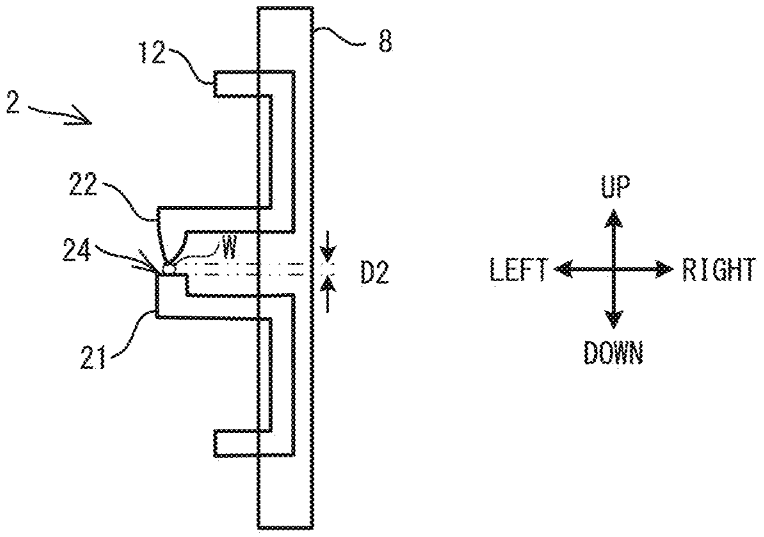
FIG. 31 is a schematic diagram of the holding portion 2 of the electroporation device 10 according to the modified example.
Figure 32:
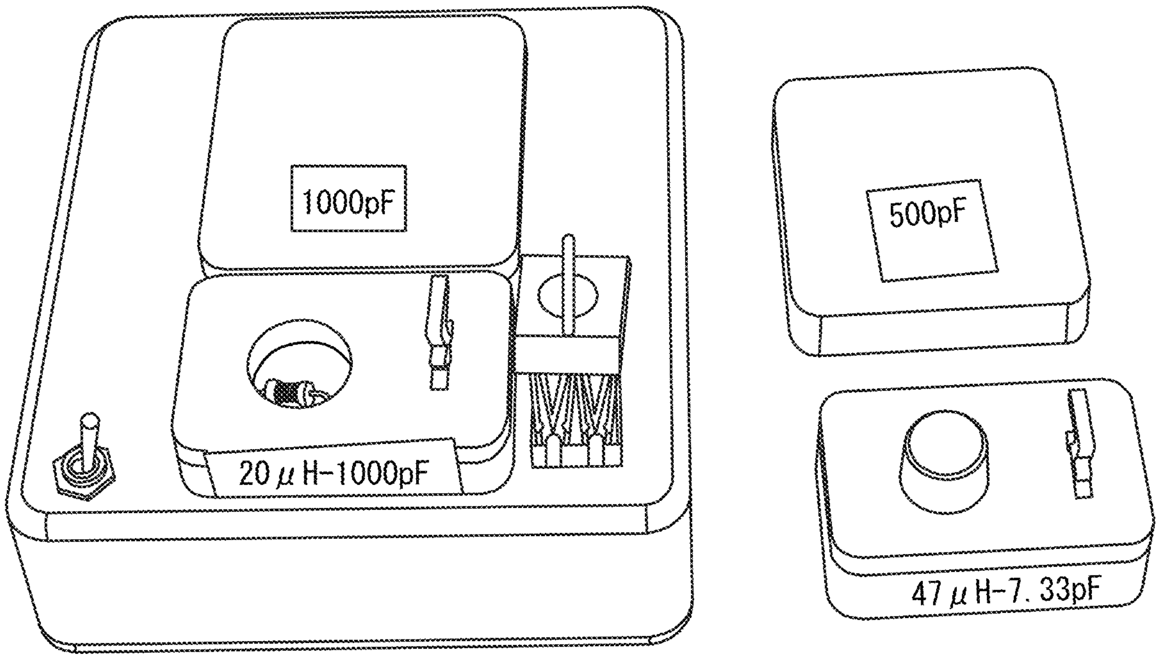
FIG. 32 is a photograph of the electroporation device 10 according to a modified example after assembly.
Figure 33:
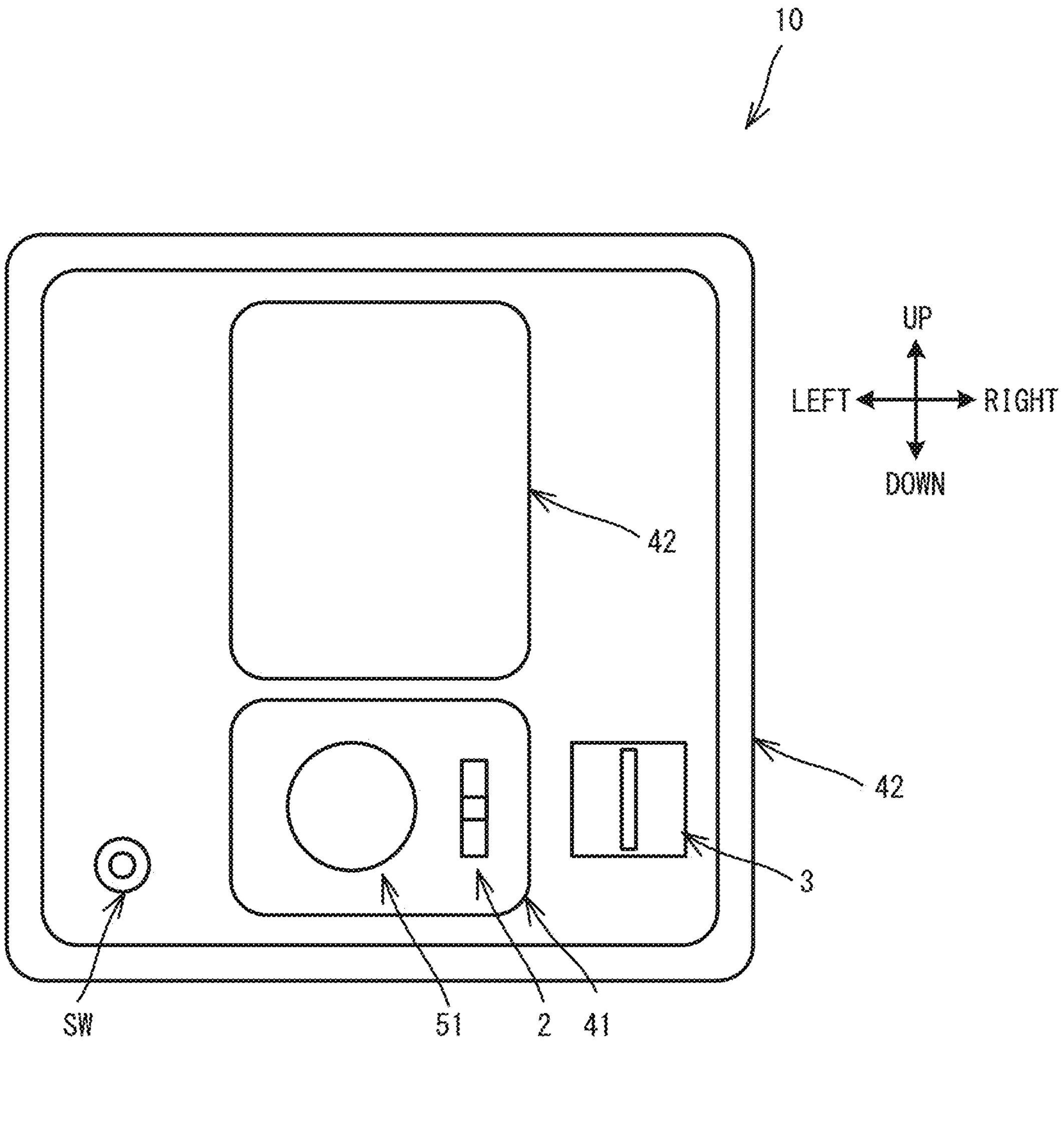
FIG. 33 is a schematic diagram of the electroporation device 10 according to a modified example.

In the electroporation device, the arrangement of the holding portion, the discharge generating portion, the conductive portion, and the power amount control portion may be changed as appropriate. For example, as in an electroporation device according to a modified example shown in FIG. 30 and FIG. 31, in the device 10 according to Example 4, the holding portion 2, the conductive portion 4, and the power amount control portion 5 may surround the periphery of the discharge generating portion 3, and may be fixed to wall surfaces extending in the up-down direction. In this case, the holding portion 2 may be provided with the pair of electrodes 21, 22 and the placement portion 24, and the pair of electrodes 21, 22 may be held in the insulating resin plate 8 with the predetermined gap D2 in the up-down direction (see a central lower portion of the photograph in FIG. 30). As shown in FIG. 31, the placement portion 24 on which the droplet W of the predetermined amount of the cell suspension is placed may be the upper surface of the electrode 21 that is disposed in a lower position, of the pair of electrodes 21, 22. In the device 10 according to the modified example shown in FIG. 30 and FIG. 31, by disposing the holding portion 2, the conductive portion 4, and the power amount control portion 5 close to the discharge generating portion 3, resistance of the conductive portion 4 can be reduced compared to the device 10 according to Example 4, and the pulsed electric current applied to the holding portion 2 can be stabilized. In the device 10 according to Example 4, the condenser 60 may be omitted as appropriate. As shown by a device 10 according to a modified example shown in FIG. 32 and FIG. 33, the device 10 may be configured by three units, namely, a droplet holding unit 41 provided with the holding portion 2, the condenser 51, and the inductor 53, an additional condenser unit 42 provided with the condenser 60, and a main body unit 43 provided with the power supply portion 6 including a power SW, the discharge generating portion 3, and the diode 54. The droplet holding unit 41 and the additional condenser unit 42 may be detachably fixed to the main body unit 43 using a magnet and the like. The device 10 may be provided with pogo pin electrodes on the upper surface of the main body unit 43 for electrical connection between the units 41 to 43, and electrodes provided in the bottom surface of the droplet holding unit 41, and electrodes provided in the bottom surface of the additional condenser unit 42 may be respectively connected via the pogo pin electrodes. In the device 10 according to the modified example shown in FIG. 32 and FIG. 33, conditions can be easily changed by manufacturing a plurality of the droplet holding units 41 in which the conditions of the condenser 51 and the inductor 53 are changed, and a plurality of the additional condenser units 42 in which the conditions of the electrostatic capacity of the condenser 60 are changed.

DESCRIPTION OF THE REFERENCE NUMERALS

1, 10: Electroporation device
2: Holding portion
3, 37: Discharge generating portion
4: Conductive portion
5: Power amount control portion
6: Power supply portion
8: Insulating resin plate
9: Cycle adjustment portion
21, 22, 31, 32, 35, 36: Electrode
23: Container
27: Oil bath
39: Power line
51, 60: Condenser
52: Dark current control portion
54: Diode

The invention claimed is:

1. An electroporation device comprising:
a holding portion configured to hold a solution containing a foreign substance and a cell;
a discharge generating portion including a pair of electrodes disposed at a predetermined gap, placed outside the holding portion, and configured to generate an arc discharge between the pair of electrodes in a space separate from the holding portion;
a conductive portion configured to electrically connect the holding portion and the discharge generating portion in series, and to supply, to the holding portion, a pulsed electric current resulting from the arc discharge generated by the discharge generating portion; and
a power amount control portion configured to control an amount of electric energy of the pulsed electric current supplied to the holding portion.

2. The electroporation device according to claim 1, wherein
the power amount control portion includes a condenser electrically connected to a power supply portion and to the discharge generating portion, the condenser being configured to accumulate an electric charge as a result of voltage applied by the power supply portion, and the condenser being configured to discharge the accumulated electric charge to the discharge generating portion.

3. The electroporation device according to claim 2, further comprising:
the power supply portion configured to supply a high-voltage DC power of 3 kV or more.

4. The electroporation device according to claim 1, wherein
the discharge generating portion is electrically connected to a power supply portion, and
the power amount control portion includes a condenser electrically connected to the holding portion, the condenser being configured to accumulate the pulsed electric current supplied to the holding portion.

5. The electroporation device according to claim 4, wherein
the power amount control portion includes an inductor connected in parallel with the holding portion and the condenser.

6. The electroporation device according to claim 5, wherein the power amount control portion includes a diode connected in parallel with the holding portion, the diode providing a forward direction in which an electric current flows from the condenser.

7. The electroporation device according to claim 4, wherein with respect to the power supply portion, the condenser is connected in series with the discharge generating portion and the holding portion.

8. The electroporation device according to claim 1, wherein in the discharge generating portion, the predetermined gap is changeable.

9. The electroporation device according to claim 1, wherein leading ends of the pair of electrodes of the discharge generating portion are formed in a hemispherical shape.

10. The electroporation device according to claim 1, wherein the power amount control portion further includes a dark current control portion configured to control a dark current generated in the discharge generating portion.

11. The electroporation device according to claim 10, wherein the dark current control portion is an electric resistance.

12. The electroporation device according to claim 1, further comprising:

a cycle adjustment portion configured to cyclically apply a voltage to the discharge generating portion at a predetermined interval.

13. The electroporation device according to claim 1, wherein the holding portion comprises:

a pair of electrodes electrically connected to the discharge generating portion via the conductive portion, wherein the solution is held between the pair of electrodes of the holding portion.

14. The electroporation device according to claim 13, wherein the holding portion further comprises a container configured to hold the solution, the container being formed of an insulating material, and the pair of electrodes of the holding portion is disposed in the container.

15. A method for producing cells with an introduced foreign substance, comprising:

a holding process of causing a holding portion of the electroporation device according to claim 1 to hold a solution containing a foreign substance and a cell;

a supply process of generating a pulsed electric current by arc discharge and supplying the generated pulsed electric current to the holding portion; and a recovery process of recovering, from the holding portion, the solution that has undergone the supply process.

16. An electroporation device comprising:

a holding portion configured to hold a solution containing a foreign substance and a cell;

a discharge generating portion including a pair of electrodes disposed at a predetermined gap, placed outside the holding portion, and configured to generate a spark discharge caused by dielectric breakdown of a gaseous medium between the pair of electrodes in a space separate from the holding portion;

a conductive portion configured to electrically connect the holding portion and the discharge generating portion in series, and to supply, to the holding portion, a pulsed electric current resulting from the spark discharge generated by the discharge generating portion; and a power amount control portion configured to control an amount of electric energy of the pulsed electric current supplied to the holding portion.

* * * * *